United States Patent [19]

Lynnworth

[11] 4,193,291
[45] Mar. 18, 1980

[54] SLOW TORSIONAL WAVE DENSITOMETER

[75] Inventor: Lawrence C. Lynnworth, Waltham, Mass.

[73] Assignee: Panametrics, Inc., Waltham, Mass.

[21] Appl. No.: 881,753

[22] Filed: Feb. 27, 1978

[51] Int. Cl.² ............................................. G01N 9/24
[52] U.S. Cl. ..................................................... 73/32 A
[58] Field of Search ................... 73/32 A, 30, 584, 590, 73/592, 54, 32 A

[56] References Cited

U.S. PATENT DOCUMENTS

| | | | |
|---|---|---|---|
| 2,998,723 | 9/1961 | Smith et al. | 73/290 V |
| 3,540,265 | 11/1970 | Lynnworth | 73/339 X |
| 3,540,279 | 11/1970 | Fam | 73/339 |

FOREIGN PATENT DOCUMENTS 206146  6/1968  U.S.S.R. ........................................ 73/54

OTHER PUBLICATIONS

"Ultrasonic Method . . ." by N. S. Ageeva from "Akusticheskii Zhurnal", vol. 6, No. 1, pp. 120–121, Jan.–Mar. 1960.
"An Ultrasonic Liquid Level . . ." by A. E. Arave, Idaho Nuclear Corp. IN 1442, Nov. 1970.
"Viscoelastic measurement . . ." by Knauss et al. from Journal of Polymer Science, Polymer Symposia No. 43, pp. 179–186 (1973).
"Industrial Applications of Ultrasound . . ." from IEEE Transactions on Sonics and Ultrasonics by Lynnworth, vol. SU22(2), pp. 71–100, Mar. 19, 1975.
"An Ultrasonic Void Fraction Detector . . ." by A. E. Arave, Idaho Nuclear Corp. IN 1441, Oct. 1970.
"Ultrasonic Liquid Level . . ." by A. E. Arave, Aerojet Nuclear Co., ANCR 1047, Jan. 1972.

*Primary Examiner*—Jerry W. Myracle
*Attorney, Agent, or Firm*—Kenway & Jenney

[57] ABSTRACT

An ultrasonic densitometer for measuring the density or a density related parameter of a fluid has at least one transducer assembly that transmits and receives torsional waves guided in an axially extending sensor that is at least partially immersed in the fluid. The sensor has a noncircular cross section, typically rectangular, with dimensions, aspect ratio, frequency and bandwidth selected to limit dispersion. This non-circularity creates an inverse and substantially linear relation between the density of the fluid and the velocity of the torsional wave in the sensor. To meet special requirements, the sensor can take a variety of forms including axially curved, axially profiled, segmented or longitudinally composite. This densitometer, alone or in combination with conventional auxiliary ultrasonic measuring systems, can measure fluid density, density profiles, liquid level, viscosity, mass flow rate, gas pressure, and boiling or condensation, including measurements of flowing fluids in small conduits.

46 Claims, 22 Drawing Figures

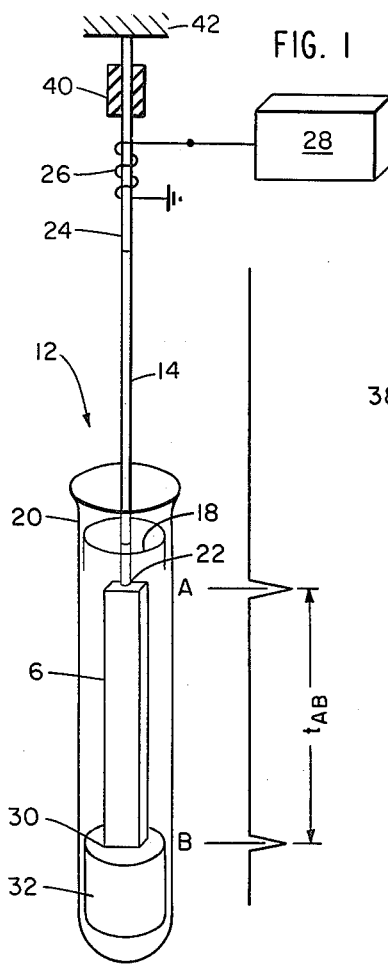
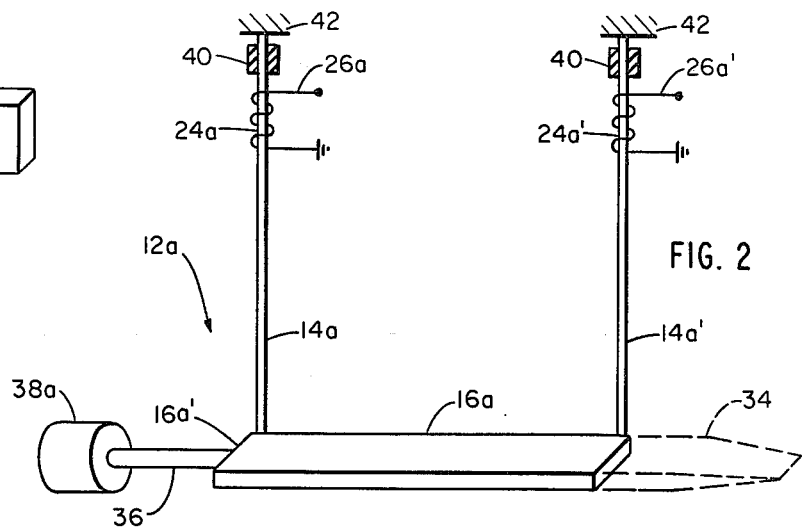
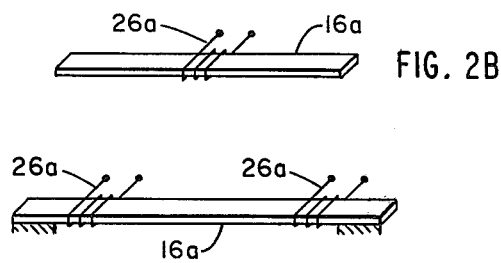
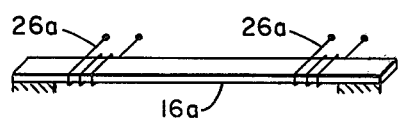
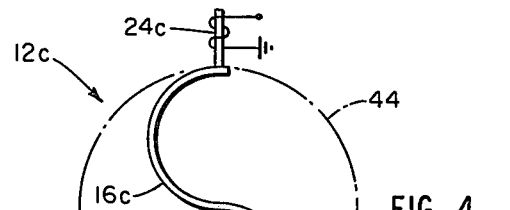
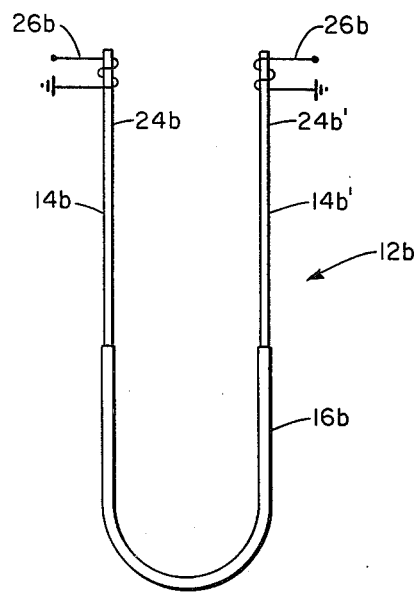
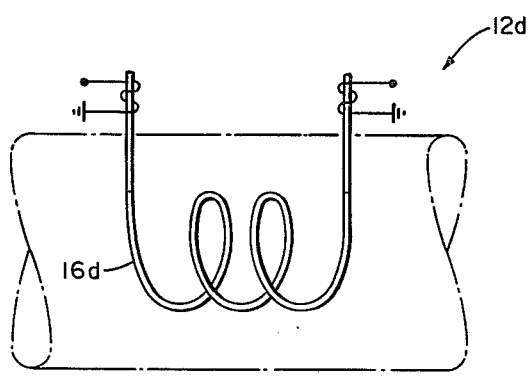

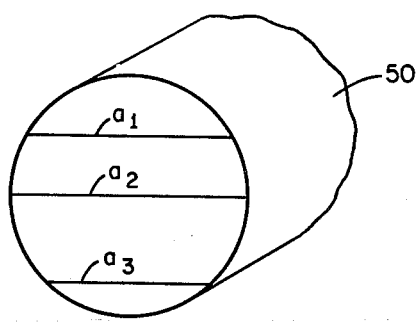
FIG. 9a
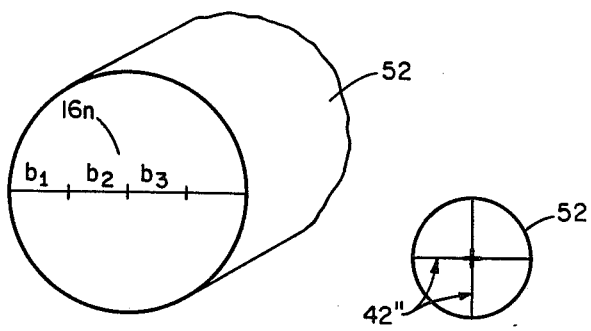
FIG. 9b
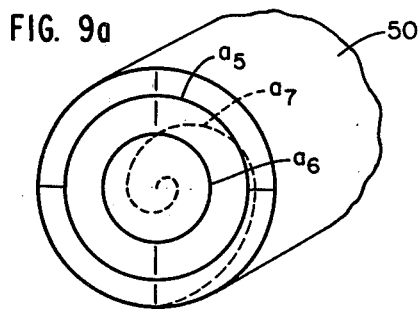
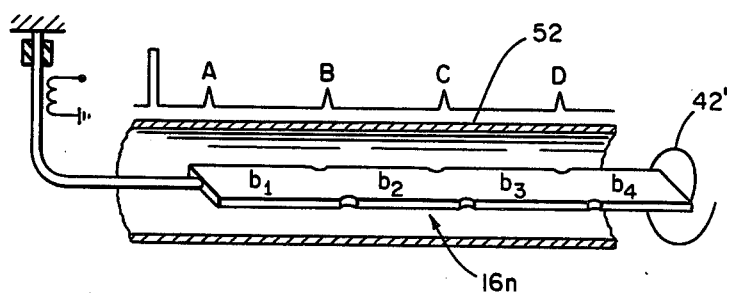
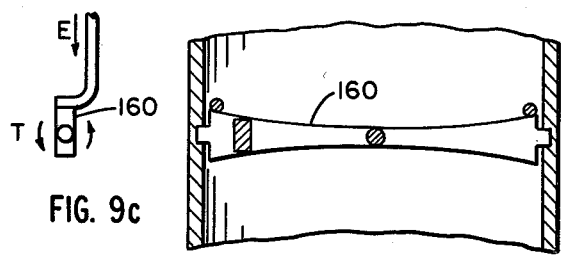
FIG. 9c
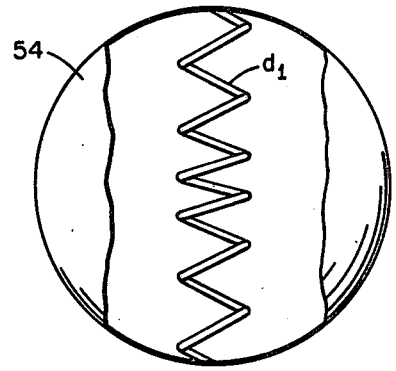
FIG. 9d
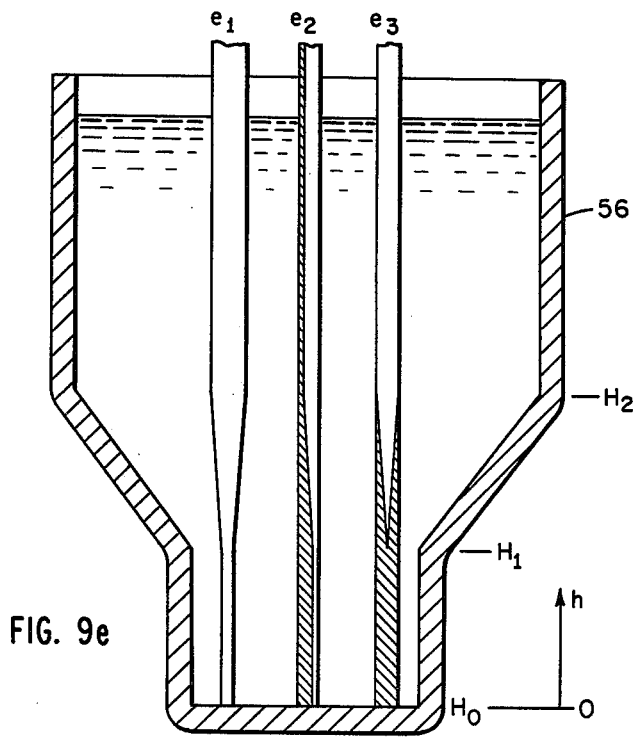
FIG. 9e
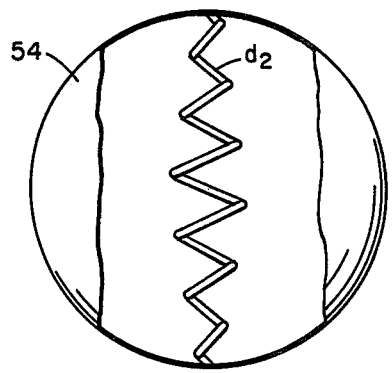

FIG. 9f
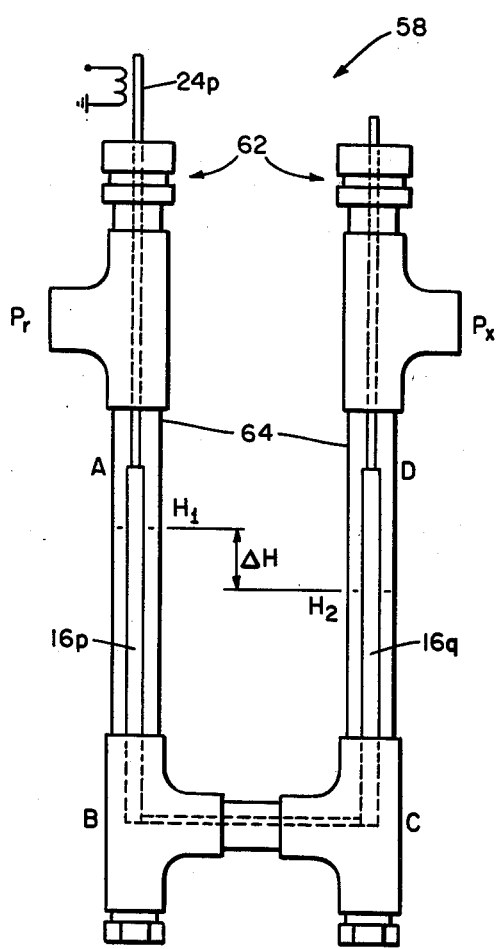
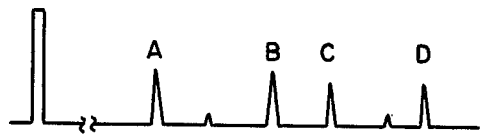
$t_{AB} - t_{CD} \propto \rho \Delta H$
$\propto (P_x - P_r)$
$\Delta t \propto \Delta P$
FIG. 9g
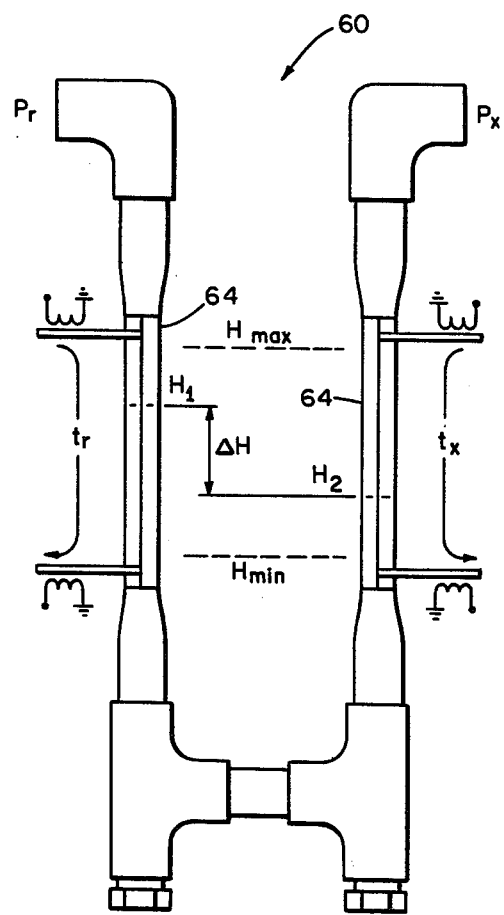
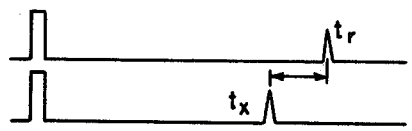
$t_r - t_x \propto \rho \Delta H \propto (P_x - P_r)$

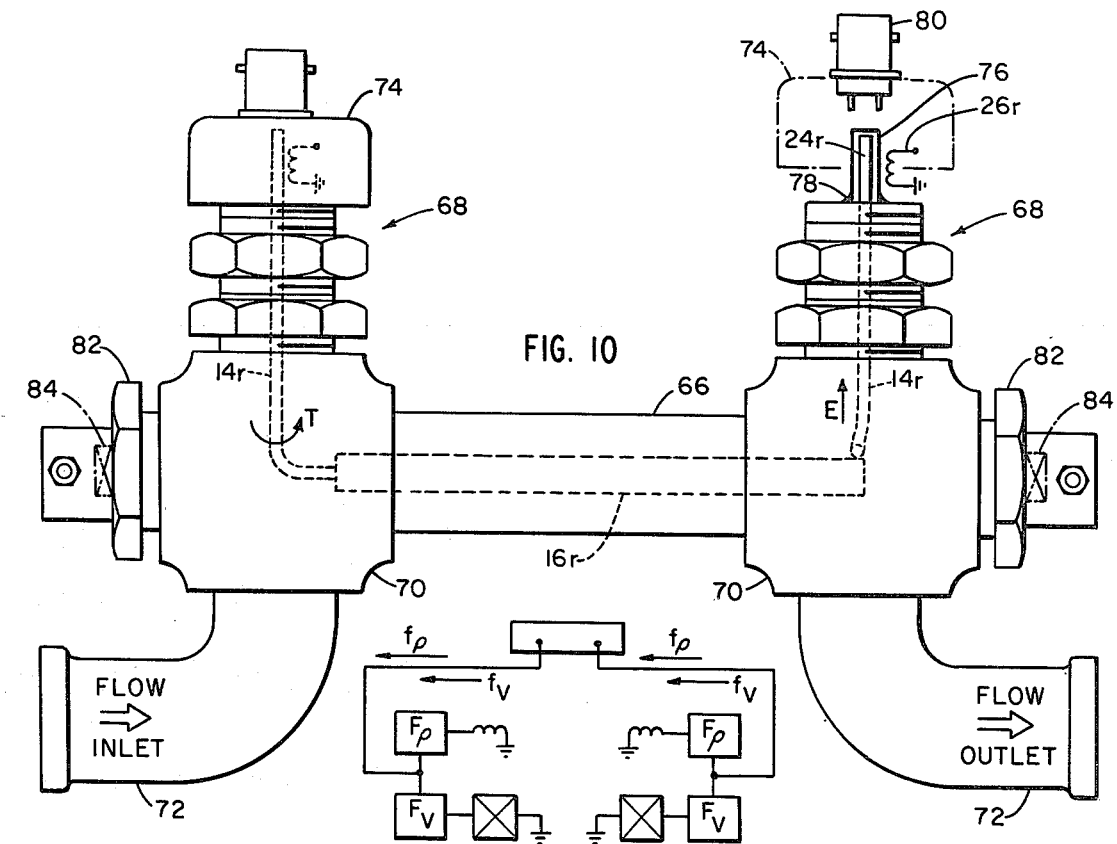
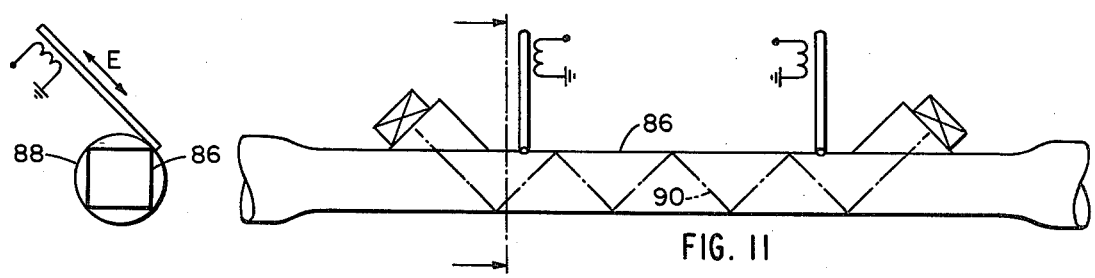
FIG. 10
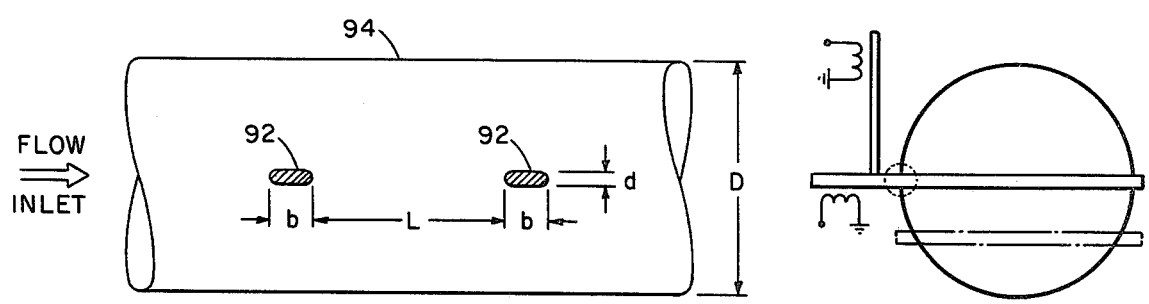
FIG. 11
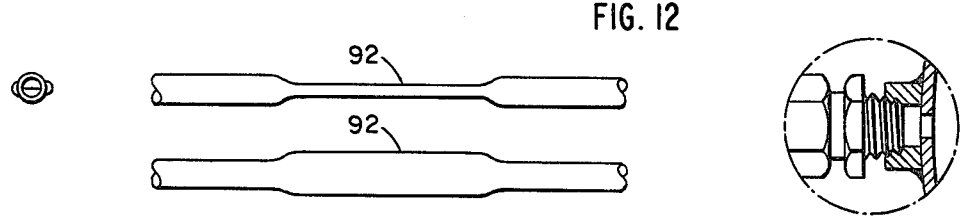
FIG. 12

SLOW TORSIONAL WAVE DENSITOMETER

BACKGROUND OF THE INVENTION

This invention relates in general to ultrasonic measurement systems. More specifically, it relates to an ultrasonic densitometer that uses slow torsional waves to measure the density or density related parameters of fluids.

There are many known methods for measuring the density $\rho$ of fluids. For liquids, the most common is an inexpensive float-type hydrometer, but it is not adequate for rapidly changing dynamic conditions or for gases. More sophisticated densitometers utilize density-dependent physical properties such as electrical conductivity, dielectric constant, or gamma-ray absorption.

Many acoustic densitometers are also known. In general, they utilize the resonant frequency characteristic of a structure such as a U-tube or a circular cylindrical shell, sometimes including a vane across a diametrical plane of the shell. Resonant shell densitometers can be highly accurate, but they are limited in application because they require a large volume of fluid (pipe diameters of 50 mm) for an accurate $\rho$ determination. They are therefore too large for convenient use in aircraft or other engine applications where the rate of fuel consumption is less than about 1 kg/sec. Likewise they are too large for use with liquids contained in ordinary laboratory test tubes. Resonant tube densitometers also provide high accuracy (about 0.1 mg/cm$^3$) but they are limited to densities less than 3 g/cm$^3$, limited in the sampling mode to low flow rates and limited to temperatures close to ambient. Also, response time, despite a small sample volume, typically less than 1 ml, is slow, ranging from 0.5 to 5 minutes.

Heretofore, in a common application, measuring fuel density in aircraft engines where very limited fuel volumes are available, a device using concentric metal tubes whose electrical capacity is proportional to fuel dielectric constant has provided the most accurate measurements. But even these capacitance tubes require a flow channel diameter of at least 20 mm and preferably over 25 mm. Other limitations are that accuracy is reduced for fuels other than JP-4 and JP-5 and if the fuel temperature ranges over too wide an extreme, e.g. from $-60°$ C. to over $100°$ C. Absorbed moisture in fuels would also degrade the accuracy, due to the disproportionate perturbation of average dielectric constant by a small quantity of water. Conductive or conductively-contaminated liquids cannot be measured by a capacitance type densitometer.

It is also known to use torsional waves in ultrasonic systems. For example, U.S. Pat. No. 2,988,723 to Smith et al discloses a sonic wave conductor to measure the level of a liquid in a tank. The conductor includes a generally cylindrical core and fins secured on its outer surface and extends vertically in the liquid. A measurement is made by detecting an echo generated at the interface of the conductor and the surface of the liquid. The fins amplify what would otherwise be a weak echo. The sound energy can be a torsional wave for some fin designs but it does not measure the density or other characteristics of the liquid. Also in this Smith system the type of sound energy, e.g. torsional or longitudinal, is not particularly significant.

In general, work with torsional waves has used waveguides having a circular cross section. However, it has been known that the velocity of a torsional wave in waveguides formed of an elastic material with a rectangular cross section is reduced by a shape factor K. This observed velocity reduction was not previously related to the density or other density-dependant characteristics of the fluid surrounding the waveguides. Characteristics of fluids have been investigated by ultrasonic wave guides, but using sound energy in vibrational modes other than torsional. For example, a reduction in the velocity of flexural waves in aluminum strips immersed in water has been reported, but there was no association between this effect and the density of the water. Later work with flexural waves demonstrated that there were significant practical difficulties due to dispersive propagation that imposed limits on probe dimensions and bandwidth. Also, depending on design and operating parameters, there can be substantial attenuation of the flexural wave energy due to its radiation into the fluid.

It is therefore a principal object of this invention to provide an ultrasonic densitometer that accurately measures the density of a wide variety of fluids including liquids, gases under high pressure, two-phase liquids plus vapor and hostile liquids in sealed containers.

Another object is to provide an ultrasonic densitometer that operates over a wide temperature range.

A further object is to provide an ultrasonic densitometer that operates rapidly and under dynamic conditions.

Yet another object is to provide an ultrasonic densitometer that measures the density or density related parameters such as mass flow rate, of flowing fluids including flow in conduits with a very small diameter.

A still further object is to provide a densitometer that operates in a pulse-echo mode or a through-transmission mode utilizing narrowband or broadband pulses.

Another object is to provide a densitometer that measures the density of a fluid along a curved path.

Still another object is to provide a densitometer that is acoustically weighted to correspond to the shape of a container or segmented to yield a density profile.

Yet another object is to provide a densitometer that measures one of a variety of parameters such as liquid level, viscosity, condensation or liquid mass in a partly filled container of arbitrary shape.

A further object is to provide a densitometer that can measure the density of a fluid with high resolution and utilizes relatively low cost electronic instrumentation.

Another object is to provide a densitometer that measures fluid density in conjunction with the measurement of at least one other parameter of the fluid.

SUMMARY OF THE INVENTION

An ultrasonic densitometer that measures the density or density related parameters of a fluid has at least one transducer that transmits and receives ultrasonic energy responding to torsional mode propagation of either narrowband waves or broadband pulses. The torsional wave is transmitted to and from a sensor that extends axially and guides the wave along its longitudinal axis in either a pulse-echo or through-transmission mode. The sensor is at least partially immersed in the fluid and has a noncircular cross section in a plane traverse to its longitudinal axis. With the noncircular cross section, the propagation velocity of the torsional wave in the sensor is reduced by the presence of the fluid. This velocity reduction is a substantially linear function of the density of the fluid. However, for some non-wetting liquids, the imaginary (attenuation coefficient) component α of the complex propagation constant γ for the wave is a more reliable indication of the integrated effect of the fluid density-immersion depth product than the real (velocity) component c of γ.

The departure from noncircularity is preferably not extreme to limit dispersion of the guided torsional wave to less than twenty percent over the bandwidth of the wave. Where the sensor has a generally rectangular cross section, its aspect ratio is preferably less than 4 and the broader dimension is less than λ/4 and preferably less than λ/10 where λ equals the wavelength of the torsional wave. The axial length of said sensor is preferably in the range of five to fifty times the wavelength of the torsional wave. The density of said sensor, in a homogeneous form, is preferably less than ten times that of the fluid to provide an acceptable level of sensitivity. In many cases, the sensor density is less than 5 gm/cm$^3$. In a composite form, the sensor is composed of two longitudinally extending materials whose densities differ by a factor of at least two. To accommodate a wide range of operating temperatures, the sensor can be formed of an isopaustic material.

The sensor can assume a variety of forms to accommodate various applications. It can be straight, curved, axially segmented to generate multiple echoes, or profiled to accoustically weight the measured parameter. In the curved form, if the diameter of curvature is less than the wavelength of the torsional wave in the sensor, the sensor arc length is less than 90°. In the segmented form, the areas of the noncircular segments and intermediate junctions control the associated reflection coefficients. The areas are selected to generate echoes at the junctions that are of generally the same magnitude.

When two sensors are positioned in a fluid flowing in a conduit, cross-correlated fluctuations in the measured velocity reduction are indicative of the flow velocity between them. Alternatively, a second sensor operating in a longitudinal energy mode can be used in conjunction with the torsional wave sensor also energized in the longitudinal mode to measure the flow velocity. The torsional wave sensor can also be used to measure liquid level. In one form, the sensor is immersed vertically in the liquid and level is indicated by the integrated density over the immersed portion. In another form, the sensor is straight and located horizontally or at an oblique angle with respect to the liquid surface at a predetermined vertical height. In yet another form, the sensor is segmented with horizontally oriented straight segments at varying heights connected by curved junction portions. To compensate for temperature variations, a reference measurement within the sensor can be made by also energizing the sensor in the extensional mode or forming a portion of the sensor with a circular cross section. In each case the travel time of an echo in the sensor provides the temperature information.

These and other features and objects of this invention will be more fully understood from the following detailed description which should be read in light of the accompanying drawings.

BRIEF DESCRIPTION OF THE DRAWINGS

FIG. 1 is a perspective view partially in section of an ultrasonic densitometer according to the invention shown measuring the density of a liquid in a test tube using a pulse-echo mode of interrogation;

FIG. 2 is a perspective view of an ultrasonic densitometer also according to the invention that is designed to operate in a through-transmission mode;

FIGS. 2A and 2B are perspective views showing alternative arrangements for energizing the sensor shown in FIG. 2;

FIGS. 3, 4 and 5 are views in side elevation of curved sensor configurations according to the invention;

FIG. 9a is a perspective view of a densitometers according to the invention positioned in two round pipes to provide an integrated average fluid density along their lengths and weighted to yield a fluid density averaged over the entire cross section of the pipe;

FIG. 9b is a view of a densitometer according to the invention positioned in a round pipe segmented sensor of the densitometer together with an associated signal diagram suitable for generating a density profile of a fluid flow in the pipe;

FIG. 9c is a view in vertical section and partially in elevation of a densitometer according to the invention positioned in a pipe and utilizing a sensor axially profiled to weight the measured density of a fluid carried in the pipe together with a detail of the lead-in coupling to the sensor;

FIG. 9d is a view of densitometers according to the invention utilizing sensors in a helical configuration with a nonuniform pitch or diameter selected to weight the integrated density of a fluid held in a spherical container to measure the fluid volume;

FIG. 9e is a view in vertical section and partially in elevation of several densitometers according to the invention having straight sensors of variable cross-sectional dimensions or of composite construction with varying longitudinal distribution of two materials used to measure the mass or density profile of a fluid held in a nonprismatic container;

FIGS. 9f and 9g are views in side elevation and associated signal diagrams of densitometers according to the invention used in manometers to make differential pressure measurements;

FIG. 10 is a view in side elevation and an associated schematic wiring diagram of a densitometer according to the invention incorporated in a pipe with standard compression fittings to form a mass flowmeter;

FIG. 11 is a view in side and end elevations of a densitometer according to the invention where the sensor is a thin-walled conduit; and FIG. 12 is a view in side and end elevations, with details of the sensors and lead-in coupling, of a densitometer according to the invention utilizing a pair of straight sensors positioned in a fluid flow in a pipe to measure the flow velocity or the mass flow rate.

DETAILED DESCRIPTION OF THE PREFERRED EMBODIMENT

Figure 6A:
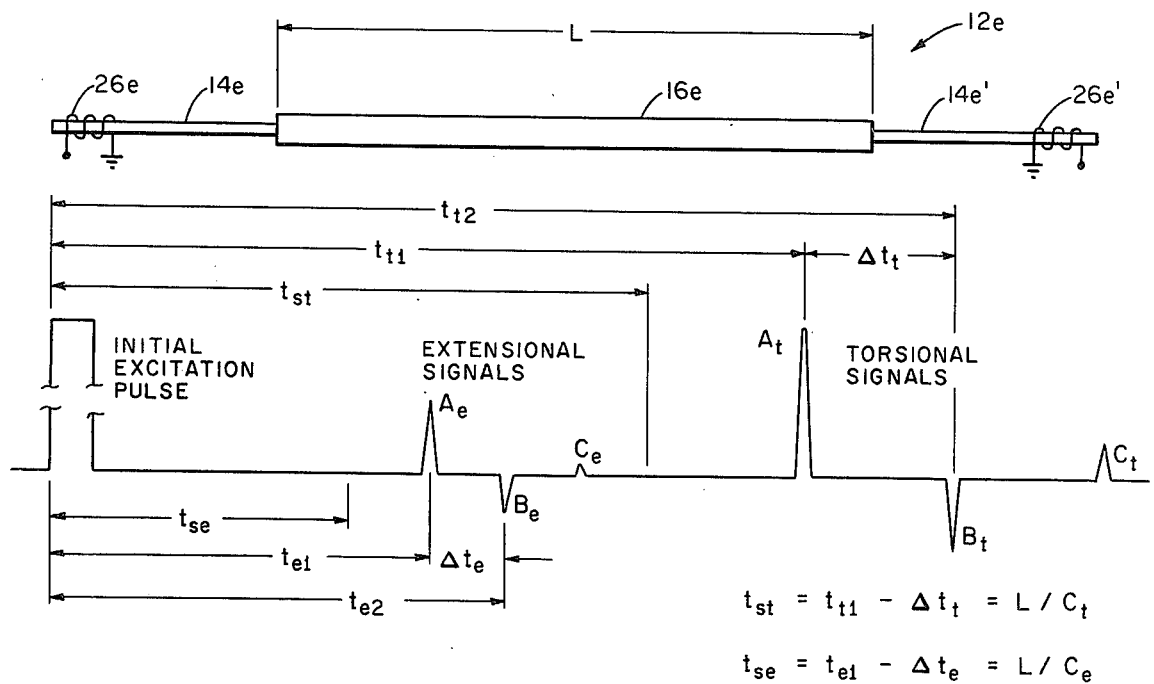
FIGS. 6a and 6b are views in side elevation together with signal diagrams of alternative densitometer configurations according to the invention for compensating for the effects of variations in temperature and viscosity, respectively.

Underlying the densitometer of this invention is the discovery that if a noncircular waveguide or sensor for a torsional ultrasonic wave is immersed in a fluid then the complex propagation constant $\gamma$, including a real velocity part c and an imaginary attenuation coefficient part $\alpha$, ($\gamma = c + i\alpha$) is a substantially linear function of the density of the waveguide, the integrated density of the fluid and the degree of noncircularity of the waveguide. For most fluids, the real velocity is the more reliable part, and therefore this discussion will usually refer only to a velocity reduction due to the adjacent fluid. (For certain non-wetting liquids, the imaginary (attenuation) part is a more reliable indication than the real (velocity) part.) More specifically, the magnitude of the fractional reduction of the velocity, $|\Delta c/c|$, is approximately directly proportional to the fluid density $\rho$ and to the degree of noncircularity, but is inversely proportional to the density $\rho_s$ of the sensor. This relationship does not hold if the fluid deposits significant residues on the waveguide. The noncircularity is quantified by a shape factor K which is less than unity. Since the torsional wave propagated in a noncircular waveguide will always be slower than in the same material formed in a circular waveguide the wave is termed "slow". It should be noted that this slowing occurs even in a vaccuum and that the presence of a fluid adjacent the waveguide further slows the wave.

Although a theory does not yet exist to quantitatively account for the observed dependence of $\Delta c/c$ on $\rho$, $\rho_s$ and K, it is known that in vacuum, the torsional waves propagate at the velocity $c_t = K\sqrt{G/\rho_s}$ where G = shear modulus and $\rho_s$ = waveguide density. When a waveguide of rectangular cross section is immersed in an ordinary liquid of density $\rho$, the added inertia further reduces the velocity: $\Delta c/c_t \approx (\rho/2\rho_s)(1-1/K)\%$. For partial immersion, the increase in transit time $\Delta t$ is proportional to the wetted length H. These relationships have been investigated with sensors of materials with $\rho_s = 1$ to 20 g/cm$^3$ at 100 kHz using broadband or narrowband torsional waveforms transduced magnetostrictively in pulse-echo and through-transmission modes; in straight, curved and in right-angle configurations and in liquids of $\rho \approx 0.6$ to 13 g/cm$^3$ including N$_2$ at $-196°$ C., Hg at 27° C. and Pb above 327° C.

With these latter two liquid metals, tests were conducted in air, with no special provisions made to prevent oxidation or an air film between graphite or stainless steel sensors and the liquid. In these cases, wetting was apparently incomplete, and although phase shift and amplitude effects were observed upon immersion, the data did not fit the empirical equation for $\Delta c/c$ stated previously. Exceptions to the empirical equation also were noted for a fused silica sensor immersed in glycerol cooled to 6° C. At 6° C., glycerol's viscosity $\eta$ is about 10 poise ($\sim 1000$ times higher than ordinary water). This not only attenuates the guided torsional wave but also apparently creates sufficient drag to increase the change in the wave travel time $\Delta t$ by about 20% over that predicted by the empirical equation.

It is also useful to consider the impedance characteristics of junctions between elements transmitting torsional waves. Consider a densitometer 12 as shown in FIG. 1 having a straight circular lead-in 14 coupled to a substantially rectangular sensor 16. The reflection and transmission of energy at the lead-in/sensor joint are governed by the torsional wave impedances $Z_o$ and $Z_\phi$. For the circular lead-in, $Z_o = \rho_1 c_1 J_1$ where $J_1 = \pi D^4/32$. For the sensor, $Z_{100} = \rho_2 c_2 J_2$ where if the sensor is rectangular and of cross sectional dimensions b and d, then $J = (1/12)(b^3 + bd^3)$. In vacuum, $c_2 = K\sqrt{G_2/\rho_2}$. A feature of this invention is that for bd = constant, J increases as b/d increases, but K does almost exactly the opposite. This means that at a joint between materials of about equal torsional wave characteristic impedances, by matching areas one essentially matches torsional impedances. Further, if both materials have about the same Poisson's ratio $\gamma$, then by matching areas one will essentially match impedances for both torsional and extensional modes. As a corollary, a desired degree of impedance mismatch is achievable by means of controlled area mismatching.

One other theoretical consideration, dispersion, should be mentioned prior to a discussion of various preferred densitometer configurations according to this invention. It appears that dispersion of broadband pulses becomes increasingly prominent and troublesome if $b > \lambda/10$ and if sensor length L exceeds $\lambda$. Thus, to avoid these problems, a useful design guide is: operate at a frequency low enough and b narrow enough so that $\lambda$ will exceed b by a factor of about 10. If this is not practical L should be minimized and/or broadband pulses avoided, if consistent with other requirements.

In many sensor designs it will be convenient but not essential to minimize dispersion by minimizing b/d, b/$\lambda$, d/$\lambda$ and sensor length L, while retaining adequate sensitivity (which increases as b/d increases). Keeping b/d in the range 2 to 4 is often convenient, with L several times larger than $\lambda$. This generally keeps the velocity change below 20% across the bandwidth containing most of the pulse's energy even if b slightly exceeds $\lambda/10$.

Empirically, when operating slow torsional wave sensors in the vicinity of density boundaries if it is desired to avoid interaction with a density interface, there is a minimum gap that should be maintained between the sensor and the interface. This gap has been found to be comparable to b/2, typically only a few mm in water and other liquids, for broadband pulses of center frequency f $\approx 100$ kHz. Since this gap value is so small, it will be understood that a sensor of b $\leq 5$ mm, d $\approx 1$ mm, may be centered in a conduit of relatively small diameter, about 10 mm, without errors due to conduit wall proximity effects.

The sensitivity S of a slow torsional wave density sensor may be defined by $S = |\Delta c/c|$ for immersion in distilled water at room temperature. For $|\Delta c/c|$ much less than one, the approximation $\Delta c/c \approx -\Delta t/t$ is valid, where t is the travel time of the torsional wave in the sensor.

Tests to determine the relationship between the sensitivity of a sensor and its $\rho_s$ used identically shaped sensors, all immersed in water, but formed of materials whose density ranged from 1.2 to 19.52 gm/cm$^3$. It was found that the fractional increase in torsional wave transit time, $\Delta t/t$, was approximately inversely proportional to $\rho_s$. Thus, sensors of low density are preferred for high sensitivity, provided other requirements such as strength or chemical compatibility with the fluid are satisfied. Titanium, for example, with $\rho_s = 4.54$ g/cm$^3$, is nearly twice as sensitive as stainless steel ($\rho_s = 8.0$ g/cm$^3$).

To operate over variable temperature ranges, the sensor may be formed of a material having a negligibly small temperature coefficient of velocity. In the ultrasonic delay line art, such materials are termed thermally "isopaustic" and examples include fused silica, the refractory alloy C129 (approximately 80% Cb, 10% Hf, 10% W) made by Wah Chang of Albany, Oregon and Ni-Span-C (alloy 902) made by Huntington Alloys of Huntingon, West Virginia. A fused silica sensor can provide a density sensitivity over a hundred times greater than its temperature (T) sensitivity, for $\rho \sim 1$ g/cm$^3$ and T = ±50° C.

Torsional waves may be generated directly by piezoelectric transducers that are specially electroded, by magnetostrictive transducers using the Wiedemann effect, and indirectly by mode conversion according to the so-called Scarrot-Naylor method. All these methods, and some others, are well known in the literature. A preferred method of generating and detecting torsional waves is to use a length of wire made of the magnetostrictive alloy "Remendur" manufactured by Wilbur B. Driver Co. of Newark, New Jersey, which has been straightened by the rotating jaw process as described in applicant's article in Ultrasonics, 10(5) pp. 195–197 (Sept. 1972). That article also illustrates the simultaneous generation of torsional and extensional modes in one transducer. Some applications may require transduction at elevated temperature, at which temperature the above-mentioned torsional strain is annealed out of the Remendur. Other applications, due to geometrical or access constraints, may require lead-in and/or lead-out members to be substantially orthogonal to the sensor. In such cases, either the Scarrot-Naylor (orthogonal mode conversion) method or sharply curved lead lines may be used. For either the direct or the mode conversion methods, the magnetostrictive transduction effect at f≈100 kHz can be accomplished, if desired, across or through one or two metal sheaths each typically stainless steel, 0.25 mm (0.010") thick.

FIG. 1 shows the slow torsional wave densitometer 12 which is in a simple pulse-echo form. The sensor 16 of noncircular cross section, is shown fully immersed in a liquid 18 held in the test tube 20 where the liquid's unknown density $\rho$ is to be determined. For use at about 50 kHz, the sensor 16 may be of substantially rectangular cross section, with typical dimensions of 0.75 mm by 3 mm. Torsional waves enter and leave the sensor at the joint 22 between the sensor 16 and the lead-in member 14 whose length typically exceeds that of the sensor by a factor of two or more. The joint 22 can be secured with an epoxy adhesive, a cement, or by welding, brazing or soldering. Transducer 24 and the lead-in 14 are portions of a straight magnetostrictive Remendur rod that is typically 1 m long and 1.6 mm in diameter. The transducer portion 24 whose length may range from 10 mm up to 1 m or longer, is typically encircled by the coil 26 at a convenient location. An electronic instrument 28, preferably a pulser/receiver and time intervalometer such as the Panatherm ® 5010 manufactured by Panametrics of Waltham, Massachusetts provides an excitation pulse of about 1 to 100 μs duration. Echoes A and B generated by a controlled impedance mismatch at the lead-in/sensor joint 22 and at the other end 30 of the sensor, respectively, are processed by the instrument such that the round trip time in the sensor, $t_{AB}$, is measured to an accuracy of 100 ns or better, with 10 ns or better achievable in some cases. The amount that $t_{AB}$ exceeds the round trip time for this sensor when dry, is proportional to $\rho$.

In certain applications the sensor material can be selected so that t is not a function of temperature. The aforementioned delay line materials Ni-Span-C, the Cb alloy C129, fused silica as well as high density impervious graphite are suitable. For other sensor materials such as stainless steel 304, aluminum 6061, titanium, platinum, iridium, pyrex, acrylic or polyimide plastic, some other means of temperature compensation is required for very high accuracy determination of the fluid density. One compensation arrangement utilizes a thermocouple, thermistor or electrical resistivity temperature measurement combined with the known calibration of the torsional wave velocity of $c_{t\phi}$ as a function of temperature for the dry sensor. Another type of acoustic compensation may be derived from the extensional wave transit time in the sensor. Yet another may be derived from the wave travel time in a known length of circular cross section waveguide made of the same material as the noncircular portion where the torsional mode interrogates both cross sections at the same temperature.

To approximately center the sensor 16 in the test tube 20 to avoid errors due to the wall of the test tube a weight 32 is attached at the sensor's remote end 30. The weight 32 also serves as an acoustically massive termination. A solid cylindrical termination of the same material as the sensor, and of diameter about 10 mm, terminating a sensor of b=5 mm and d=1.5 mm, can provide a mismatch of about 50:1, which assures nearly complete reflection at the end 30. A typical length of sensor 20 is about 20 mm to 100 mm for use in a laboratory test tube, and up to about 1 m or more for sampling larger volumes of a fluid.

FIG. 2 shows a slow torsional wave densitometer 12a according to the invention in a simple through-transmission configuration. A noncircular sensor 16a conveys a slow torsional wave, introduced by tangential Scarrot-Naylor type mode conversion of an extensional wave at the junction with a lead-in member 14a. An extensional wave transducer 24a is encircled at its end or elsewhere by a coil 26a. A lead-out member 14a', a receiving transducer 24a' and receiving coil 26a' may be identical to the corresponding transmitting parts. For use in a fluid flowing parallel to the long dimension of the sensor, an aerodynamically contoured leading edge 34 is provided which projects beyond the active length of the sensor 16a. To resist the fluid force, the sensor may be supported behind its trailing edge 16a' by a strut 36 and acoustically massive termination 38a. (The optimum length of the strut 36 depends on several factors including acoustical parameters such as wavelength and pulse length. A typical strut length would be about 30 mm. A typical leading edge length might correspondingly be about 45 mm, but it could be shorter, about 10 mm.) If the torsional wave impedances of the strut and the sensor are comparable, nearly half the energy from lead-in 14a will detour to the terminated end of the strut and then be reflected to trail the initial forward-moving torsional wave A. This gives rise to a delayed pulse B. If the strut 36 is of circular cross section, then B will be delayed behind A by an interval $t_{AB}$ independent of the fluid density $\rho$, and so can provide an acoustically-generated temperature compensation. The time interval between the initial excitation pulse and the first signal to the receiver is $t_A$. Pulse-echo interrogation of lead-in and/or lead-out members provides echoes which can be used to subtract from this total time $t_A$ that part due to propagation in members other than the sensor 16a. For example, in a symmetrical arrangement, the travel time in the sensor is given by $t_s = t_A - t_1$ where $t_1$ = round-trip travel time between the initial pulse and the echo generated at the lead-in/sensor joint.

racy of the resonant frequency measurement will be poor.

Table I

| | | | | | |
|---|---|---|---|---|---|
| Reflection and transmission coefficients and echo ratios as a function of the impedance mismatch ratio $r = Z_2/Z_1$ | | | | | |
| $r$ | $\frac{1}{r}$ | $R = \frac{r-1}{r+1}$ | $T^2 = \left(\frac{2r}{r+1}\right)\left(\frac{2/r}{1+1/r}\right)$ | $\frac{A}{B} = \frac{R}{T^2}$ | $= \frac{R}{1-R^2}$ |
| 1 | 1 | 0 | 1 | | 0 |
| 2 | .5 | .333 | .888 | | .267 |
| 3 | .333 | .500 | .750 | | .667 |
| 4 | | .750 | .600 | .640 | .938 |
| 4.236 | .236 | .618 | .618 | | 1.000 |
| 5 | .200 | .667 | .556 | | 1.201 |
| 6 | .167 | .711 | .490 | | 1.458 |
| 7 | .143 | .750 | .438 | | 1.714 |
| 8 | .125 | .778 | .395 | | 1.969 |
| 9 | .111 | .800 | .360 | | 2.222 |
| 10 | .100 | .818 | .331 | | 2.474 |

It may sometimes be desirable to have the sensor generally orthogonal to the lead-in and/or lead-out, and yet avoid the asymmetry of the mode conversion eccentric right-angle joint of FIG. 2. In this case, the lead-in and lead-out can be sharply curved through a 90° bend with a radius of curvature of about 6 mm without excessive dispersion or degrading of 100 kHz pulse shape. Thus FIG. 2A shows the sensor 16a orthogonal to the main axis of the adjacent member(s), yet only one mode, the torsional mode is used throughout, without the need for mode conversion.

In FIGS. 1 and 2 a sound absorbing material such as rubber or adhesive tape acts as a dampener 40. Supports 42 can be springs to keep the sensor taut (FIG. 7) or a tight-fitting rubber stopper which combines damping and support functions. Many other arrangements obviously can achieve these objectives.

The densitometers 12 and 12a have been described in terms of non-resonant operation and broadband travelling wave interrogation, as opposed to resonant operation and narrowband standing wave techniques. Structural integrity considerations generally favor a sensor and probe construction which is more amenable to nonresonant than resonant operation. This may be explained as follows. Consider the pulse-echo sensor of FIG. 1. Comparing the impedance ratio $r = Z_2/Z_1$ at the lead-in/sensor joint for resonant and nonresonant operation, a high Q (sharp resonance) sensor ordinarily associated with resonant operation requires a large value (about 10 to 50) for r or its reciprocal. On the other hand, a low Q associated with making sensor echoes A and B of approximately equal magnitude requires that $r < 4.2$. If the lead-in and sensor are both fabricated of the same material or different materials but of comparable characteristic impedances a large r (or large 1/r) implies a large discontinuity in sensor cross sectional area and/or shape. This in turn implies a stress concentration. In applications where flow, corrosion, vibration or shock loads will be experienced, stress concentrations will lead to premature failure of the structure.

Table I shows that for where the magnitude of the echo ratio is less than two, for a sensor as in FIG. 1 then r must be between about 3 and 8, or between their reciprocals, 0.333 and 0.125. Selecting $r=3$ yields a reasonable echo ratio, $|A/B| = \frac{2}{3}$. Structural considerations will often favor a still smaller r, even at the expense of relatively unequal echo magnitudes. A similar analysis applies to the through-transmission sensor of FIG. 2. If the r's are not large enough at both ends to sustain a high Q, then resonance will not be sharp and the accu- Special cases of FIGS. 1 and 2 occur when the sensor is an electro-acoustic material, e.g., Remendur. In these cases electromechanical coupling may be made directly to the sensor. For example, if the sensor is a strip of Remendur, coil(s) may be positioned at the center, at nodal points of the dominant bending mode, or at the ends as shown in FIG. 2b. Dampeners, massive termination(s), or coil bobbins, may serve as the support means. Small pins (not shown) can provide axial restraint if required. In some of these special isolated sensor configurations, there is no stress concentration at end boundaries where r (or its reciprocal) has a very large value, theoretically an infinite value. However, undamped resonances in the sensor could lead to fatigue failure within the sensor itself. Proximity effects due to the boil bobbin, or restraint means, constitute additional undesirable attributes of the "sensor alone" concept.

Travelling waves, which are generally preferred over standing waves, are usually associated only with short pulses, i.e., pulse durations typically shorter than the round trip time in the sensor. However, in FIG. 1 or 2, for example, if one-way attenuation in the sensor is greater than about 10 dB, then continuous waves may be introduced into the sensor without setting up any significant standing wave pattern. Thus it will be understood that the electronics 28 in FIG. 1 can provide not only broadband impulses, rectangular pulses or rf bursts, but also continuous waves. For use with the densitometer 12a, well known electronic measurement techniques can be used to give the phase difference between transmitted and received rf or cw waveforms. Electronic techniques are also known for adjusting the transmitted frequency to maintain a particular phase relationship between transmitted and received waveforms, e.g., orthogonality (90°) or out-of-phase (180°) relationships. For these techniques, the instrument 28 can be similar to Panametrics' model 5051RF.

Another advantage of travelling wave methods over standing wave (resonance) methods is the former's applicability to cases where the attenuation coefficient α in the sensor is high, for example where the fluid is viscous, operation is at very high temperature (typically above the sensor's recrystallization temperature or above half its absolute melting point); or the sensor material is inherently attenuating such as a plastic. With high attenuation propagation over only one or a few traversals of the sensor can measure the travel time or the phase of a travelling wave. Thus, denoting the sensor length by L, the total attenuation can be controlled by limiting the term $n\alpha L$, where n=number of traversals, preferably to under 20 dB. Since the travelling wave term n corresponds to Q of the resonance case, a situation demanding that n be small (1 to 5), corresponds to a "resonance" situation of very low Q, where resonant frequency would be unsharp. Thus, the travelling wave method enables slow torsional waves to sense $\rho$ even when viscosity is at least 100 cp. Still another advantage of travelling waves over standing waves is their applicability to liquids which do not wet the sensor, but which nevertheless cause attenuation.

It will be understood that the foregoing terminology distinction between travelling and standing waves expresses a difference in degree. Practically speaking, for overlapping echoes, it is impossible to reduce the standing wave ratio to zero. For this discussion travelling waves are interpreted to include cases where echoes from the sensor's ends either do not overlap, or if they do overlap (due to use of a short sensor, a long pulse, or cw) then the ratio of the amplitude of one echo to the next shall not exceed e (2.718 . . . ). This corresponds to a Q less than about 5, and a corresponding low standing wave ratio. To simplify electronic instrumentation, configurations and frequencies are preferred that follow the above theoretical and empirical guidelines on avoiding significant dispersion across the band.

FIGS. 3, 4 and 5 show densitometers 12b, 12c and 12d, respectively, that use sensors 16b, 16c and 16d, respectively, that are smoothly curved over part or all of their length. In particular, FIG. 3 shows a U-shaped sensor 16b, attached lead-in and lead-out members 14b and 14b', transducer members 24b and 24b', and encircling coils 26b and 26b'. The curve is formed by bending around a bar of diameter about 20 mm. In FIG. 4, an S bend sensor 16c is shown. This design employs orthogonal transducers 24c, 24c' joined directly to the sensor approximately where the sensor becomes tangent to the inside diameter of a circular duct 44. The curve of the sensor 16c increases the sensor length to increase sensitivity (for a given material and aspect ratio) and allows for differential thermal expansion despite fixed end supports.

The curved sensor concept is extended to a helix in FIG. 5. While the sensor 16d is shown terminated at the transducer connections, it may extend another turn or two in either direction to provide a support connection. If the extra turns are of circular cross section, they can be used to generate a temperature compensation echo in a manner analogous to the use of strut 36 in FIG. 2. An aluminum helix of b=5 mm, d=1.5 mm, and 3 turns of diameter=25.4 mm provides a through-transmission sensitivity given by $\Delta t \sim 25\mu s$ per gram per $cm^3$. Measurement of this $\Delta t$ to 3 ns corresponds to $\rho$ sensitivity of about 0.1 milligram per $cm^3$.

Figure 6B:
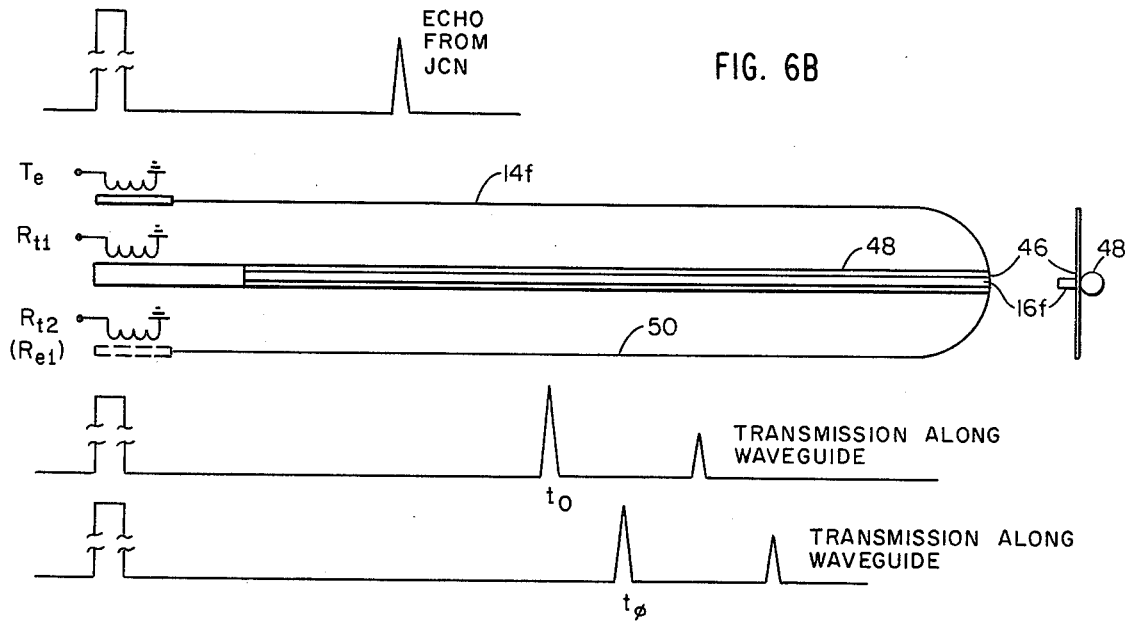

FIGS. 6A and 6B show densitometers 12e and 12f, respectively, designed to obtain the density of the adjacent fluid despite the interfering effects of one or more other variables in the fluid such as temperature T or viscosity $\eta$. In FIG. 6A, a noncircular sensor portion 16e is butt welded or silver brazed symmetrically between lead-in and lead-out members 14e and 14e'. The sensor, for example, may be stainless steel 304, and have cross sectional dimensions 0.75 mm by 3 mm (b/d=4) and a length L of 250 mm. The members 14e, 14e', for example, are Remendur with a diameter 1.6 mm and a length of 100 mm. Nickel or other corrosion-resistant plating may be applied over the Remendur or over the entire probe assembly 16e, 14e, 14e', a typical plating thickness being about 5 mm. Transmitter and receiver coils 26e, 26e', respectively, at each end are, for example, about 25 mm long and consist of 4 to 8 layers of 32 to 40 gage insulated copper wire. The transducer portions members 14e and 14e' primarily generate and respond to the torsional mode but in the presence of a weak axial field due, for example, to a small magnet, some extensional mode energy is also generated and detected. Accordingly, in the through-transmission configuration 16e, at the receiver coil 26e' one observes a sequence of voltage pulses as shown. The sequence has two parts. The extensional (subscript e) part arrives first, followed by the torsional (subscript t) part.

Turning to the effect of temperature variations on the densitometer 12e, in vacuo the effect in SS 304 of increasing T from 0° F. to 1000° F. is to increase all the $t_e$'s by about 10.5%, and all the $t_t$'s by about 11.8%. For example, if $t_{st}$ were 100 $\mu s$ at 0° F., at 1000° F. $t_{st}$ would increase to 111.8 $\mu s$, an 11.8 $\mu s$ increase due to T alone. This is about the same as the change in $t_{st}$ due to immersion of sensor 16e in water at a constant T. However, if one considers the ratio $t_{st}/t_{se}$ in vacuo, this ratio changes an order of magnitude less, only about 1.3% per 1000° F. Hence the "simultaneous" or sequential measurement of appropriate intervals as shown in the waveform schematic in FIG. 6A enables the fluid density to be computed from the "scaled ratio" $t_{st}/t_{se}$ normalized to in vacuo conditions almost completely independent of T. (This ratio compensation method would be more nearly perfect if Poisson's ratio $\sigma$ were absolutely constant over the T range.) To further compensate for the "drag" due to high viscosity liquids, additional scaling or correction terms may be derived theoretically or empirically in terms of echo amplitudes such as $A_t$, $A_e$, etc. or their ratios $A_t/A_e$, $(1/L) \ln (A_t/A_e)$, etc. One advantage of the illustrated through-transmission configurations over pulse-echo alternatives is that they may be designed to be relatively insensitive to reflective supports along the assembly.

FIG. 6B shows another through-transmission densitometer 12f in a folded format. An extensional mode is generated at coil $T_e$ and introduced via lead-in 14f. At junction 46 it is mode converted to torsion in noncircular sensor 16f and circular compensation member 48. Member 50 may provide additional support and/or additional extensional mode data if optionally terminated with a receiving transducer $R_{el}$. Analysis similar to that detailed above explains the sequence of pulses received at coils $R_{t1}$, $R_{t2}$ and drawn for this configuration, from which the fluid density $\rho$ may be determined despite potentially interfering effects of T and $\eta$.

It will be understood that T compensation does not require the basis for the "compensating" measurement to be immune to $\rho$. [Due to "hydrodynamic mass" effects the extensional wave velocity in a smooth, uniform waveguide increases very slightly upon immersion in a liquid of density $\rho$, depending on $\rho s$ and $\sigma$ in the waveguide.] For example, suppose two intervals $t_e$ and $t_t$ are measured, each being linear functions of $\rho$ and T:

$$t_e = W\rho + XT$$

$$t_t = Y\rho + ZT$$

These two equations may be solved for the two unknowns $\rho$ and T in terms of the measured $t_e$ and $t_t$ and the constants W, X, Y, Z which may be determined by calibration or computed from theoretical considerations.

The "scaled ratio" mentioned earlier leads to ρ as follows:

$$\rho = K'[(t_{st}/t_{se})_{immersed}/(t_{st}/t_{se})_{in\ vacuo}]$$

where K' is a constant depending mainly on sensor cross section.

Again, for very narrow T ranges or if the sensor is made of a low T-coefficient material, ρ can be obtained more easily from $t_{st}$ as defined in FIG. 6A. The alternate mode or alternate sensor(s) 16e, 16f might then be used to periodically calibrate the electronics. Another use of dual parallel sensors as in FIG. 6B, but with both 46 and 48 being noncircular, is to allow optimization of each sensor for widely different conditions. Further, when T and η pose no problem, densitometer 12f can measure ρ by merely scaling the torsional wave time difference $t_\phi - t_o$ obtained by comparing transmissions over noncircular and circular paths 46 and 48, respectively.

The discussion thus far has assumed the fluid to be single phase and homogeneous. However, two-phase fluids often occur due to vaporization, boiling, cavitation or other reasons. For purposes of explanation the simplest two-phase case probably is a liquid in a partly-filled tank where only part of the sensor is immersed in the liquid, the rest of the probe being exposed to the vapor phase above the liquid as shown in FIG. 7.

Figure 7:
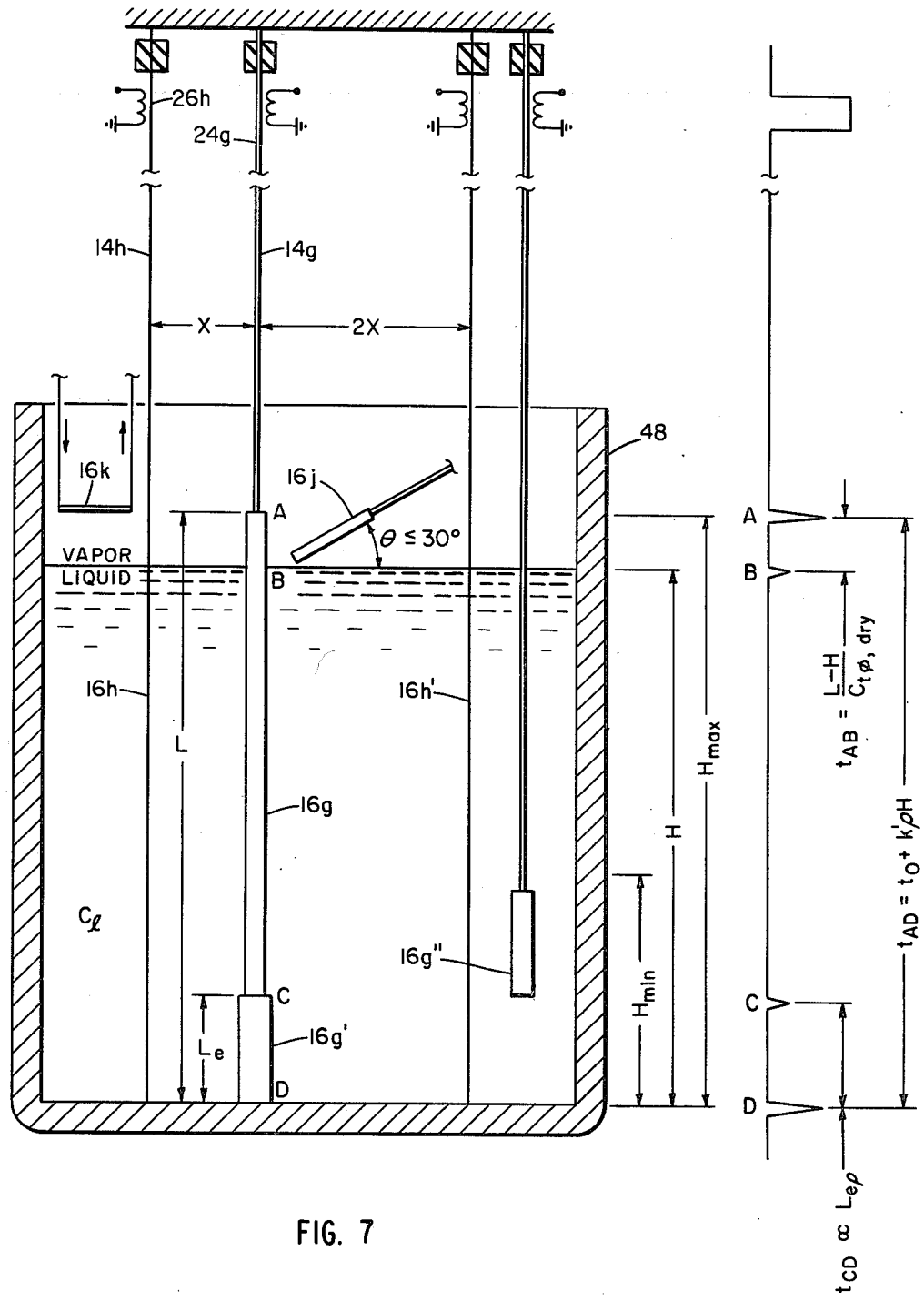
FIG. 7 is a view in vertical section and partially in elevation together with signal diagrams showing several alternative densitometer arrangements according to the invention useful in measuring the liquid level in a tank.

In FIG. 7, a container 48 is filled to level H with a homogeneous liquid of unknown ρ. A vapor phase at or near atmospheric pressure blankets the liquid. The level stays between $H_{min}$ and $H_{max}$. A sensor 16g is homogeneous, of uniform b/d, and of length L greater than or equal to $H_{max}$. It is oriented vertically and may be attached to the tank bottom or to some other convenient point of known height. The container 48 is prismatic and its axis is vertical. For the conditions specified it may be shown that the increase in transit time in the sensor, Δt, is given by $$\Delta t = k \int_0^H \rho\, dh = k\rho H = kM$$

where k=a calibration constant and M=liquid mass. This expression neglects the negligible contribution of delay due to the vapor density $\rho_v$ times the nonimmersed sensor portion L-H. If the liquid mass M remains constant while the liquid changes temperature, the fractional changes in ρ and H are equal but of opposite sign and the ρH product remains equal to M. In other words, the sensor 16g, when only partly immersed, functions as an integrating densitometer. The sensor also responds to a density-related parameter, M.

While M alone is useful and sufficient in many instances, there are nevertheless cases where it is desirable to know ρ and/or H separately. The sensor 16g has therefore been drawn in FIG. 7 to include an end portion 16g' of length $L_e < H_{min}$ which is always immersed. It has the same shape factor K as the rest of the sensor since it has the same aspect ratio b/d, but it has a dissimilar J and a correspondingly dissimilar $Z_t$. If a torsional wave pulse enters the sensor 16g echoes are generated at the top and bottom of end portion 16g'. The time between these echoes, $t_e$, provides a measure of ρ independent of H. Alternatively one could use a second short sensor such as 16g" instead of utilizing the fabricated impedance discontinuity in sensor 16g.

Because $(c_{t\phi})_{wet}$ in the immersed portion of sensor 16g is different from $(c_{t\phi})_{dry}$ in the nonimmersed portion, the torsional wave impedance in the waveguide has a discontinuity where the sensor intersects the liquid surface at level H. The step usually is small, and so the reflection coefficient usually is also small.

The signal or waveform diagram accompanying the apparatus in FIG. 7 shows schematically the important echoes. It will now be understood that a sequence of time interval measurements will yield the data necessary to calculate H and ρ, and of course ρH.

An alternate way of determining H independent of ρ while using the same ρ sensor 16g combines one or two additional probes 16h and 16h'. Transducer 24g is operated (biased) to launch simultaneously both torsional and extensional modes as discussed above. Probe 16h is responsive to the extensional mode. If the gain of the receiver (such as the electronic instrument 28 of FIG. 1) is increased sufficiently, typically to about 60 dB, a weak liquid-borne pressure wave transmitted sideways from sensor 16g due to the Poisson effect can be detected and reciprocally induced to launch an extensional wave in member 16h. Here the instrument 28 is operated in the through-transmission mode, connected to transducers 24g and 24h attached to the lead in members 14g and 14h. The observed through-transmitted time interval includes the liquid-borne delay $c_l x$ where x=distance between the probes 16g and 16h. If x=25 mm this delay $t_l$ would be about 16 μs for ordinary water, corresponding to a waveguide path length of perhaps 75 mm and a liquid level increment of half that, or 37.5 mm. If higher accuracy is desired, $t_l$ can be calculated or measured. If the second extensional probe 16h' is spaced a distance 2x from sensor 16g, the difference in liquid travel times will exactly equal $t_l$. This differential path, 3-probe method not only yields ρ and H, but also $c_l$, provided the separation x is known. $c_l$, in turn, may sometimes be related to composition, temperature, pressure or other liquid properties.

FIG. 7 also shows two special sensor orientations which may be considered special cases of the designs of FIGS. 1 and 2. In one, a sensor 16j interrogated in pulse-echo mode, is acutely angled at θ≦30° relative to the liquid surface. The angling increases the sensitivity to changes in level. As the level rises ΔH, the wetted length increases as the secant of θ. This result is further exploited by the through-transmission configuration represented by sensor 16k.

Sensor 16k is oriented horizontally with its larger faces parallel to the liquid surface. For b/d≈3, when the liquid level rises to wet one large horizontal face, the transit time suddenly increases. If the level continues to rise, a second and similar sudden increment is observed when the second large face is immersed. A sensor 16k of stainless steel with b≈5 mm, d=1.5 mm, and interrogated with a broadband pulse of center frequency f=0.1 MHz, appears to be "fully immersed" when submerged to a depth of 3 mm or more. If the liquid surface is ripple-free, H resolution to a fraction of a millimeter is achievable easily.

Figure 8A:
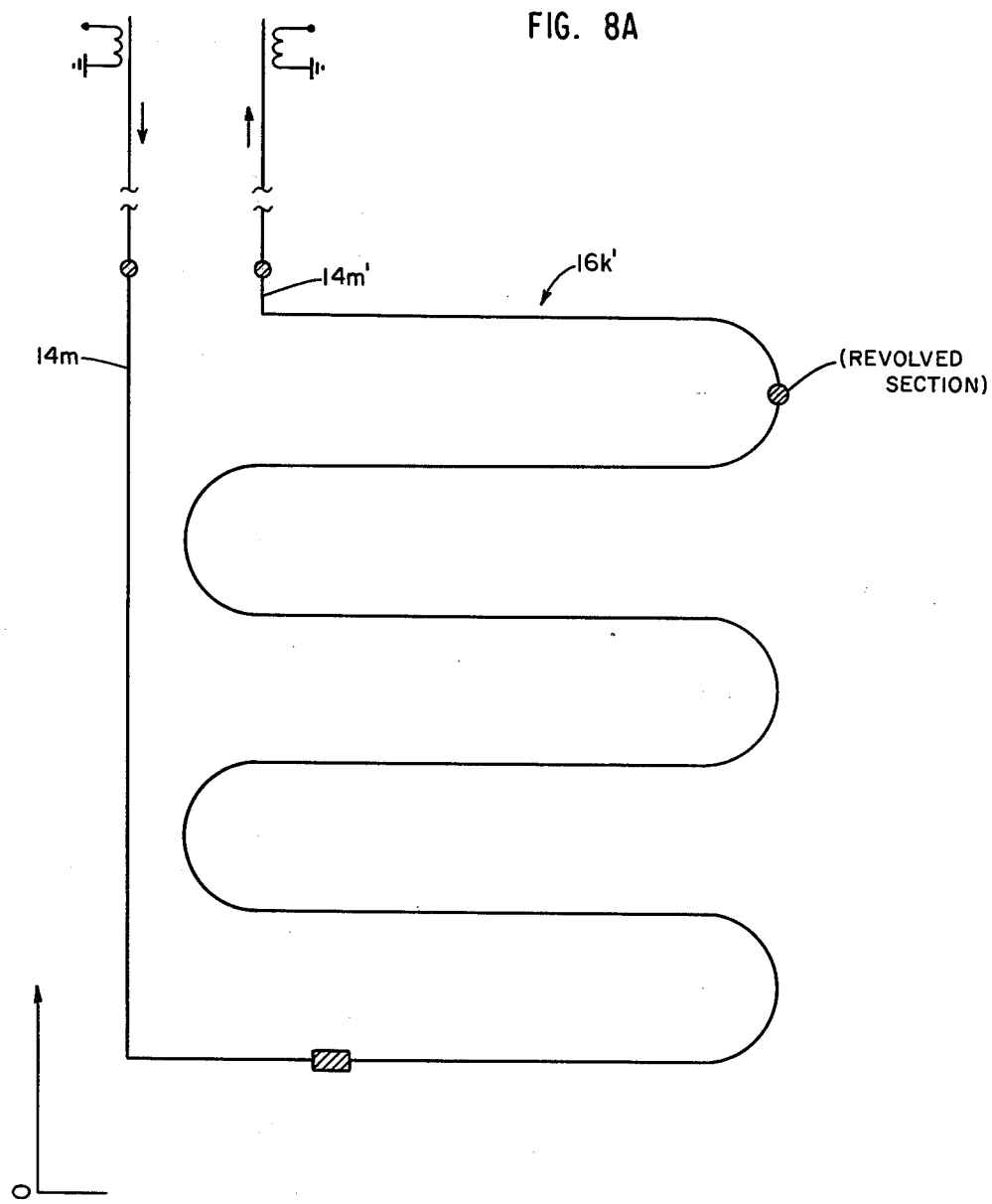
FIG. 8A is a view in side elevation of an alternative densitometer configuration according to the invention for measuring liquid level.
Figure 8B:
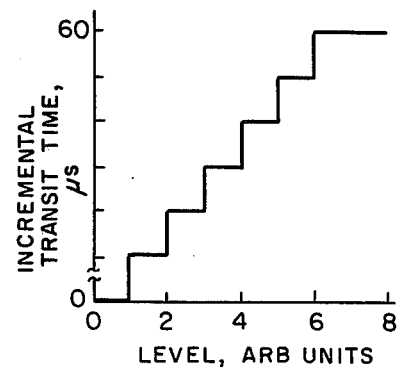
FIG. 8B is a graph showing the incremental signal travel time in the sensor of FIG. 8A as a function of the liquid level.

FIG. 8A shows a sensor 16k' that is segmented into horizontal noncircular portions as shown. The lead-in and lead-out members 14m, 14m' are of circular cross section. Likewise the semicircular curves between sensor portions are of circular cross section. This design provides significant increases in transit time as each step is wetted, analogous to the operation of the sensor 16k, yet is nonresponsive to level changes between steps. For example, one can arrange b/d and the sensor material such that $\Delta t \approx 10$ μs per step when wetted by water, or a total of about 60 μs when the entire 6-step staircase is immersed (FIG. 8b). This design is fairly tolerant of a temperature-dependent shear modular since, for example, the 10 μs steps in $\Delta t$ are so distinct that ±0.5 μs deviations per sensor portion due to temperature or to mechanical tolerances on b and d can be disregarded. The sensor 16m may be formed by collapsing portions of a circular tube into the noncircular segments while retaining the circular cross section for the semicircular connecting curves.

For all of the foregoing sensor configurations, there are several factors influencing a selection of preferred dimensions for the sensor and its interaction with the instrument 28. The aspect ratio b/d generally should be kept small, less than about 4, to avoid dispersion. Sensor length $L_s$ should be adequate to obtain the required sensitivity consistent with constraints imposed by the sensor density $\rho_s$, the liquid density $\rho$ and the resolution of the electronics. On occasion, space, structural integrity considerations, material constraints and sensitivity requirements will dictate the need for higher b/d with correspondingly higher sensitivity, say b/d from about 4 to 10. If f is high, this implies dispersion, which in turn implies the use of a narrowband pulse or a fixed frequency continuous wave. If the resonant frequency of a dispersive sensor is measured, then upon immersion its frequency would change due to $\rho$, but at this new frequency the sound speed would be different not only because of $\rho$ but also because of the different frequency per se. While these considerations do not by themselves rule out a resonant measurement, in general simpler and easier to interpret results are obtained through the use of fixed frequency techniques, e.g., time intervalometry between broadband pulses (bandwidth $\gtrsim 50\%$) when propagation is not dispersive, or phase difference (or group delay) of narrowband (bandwidth $< 10\%$) rf fixed frequency bursts which are appropriate even if propagation is dispersive.

In discussing FIG. 7 it was assumed for simplicity that $\rho$ was constant throughout the liquid. Normally, however, due to temperature gradients and thermal expansion or contraction, $\rho$ stratification occurs, especially in stagnant pools and even in fluids flowing under laminar conditions. Several ways of dealing with $\rho$ profiles are shown in FIGS. 9a, b, c, d, e, f, g.

In FIG. 9a a multiplicity of $\rho$ sensors $a_1$, $a_2$, $a_3$ are shown positioned in one round pipe 50 with their axes in a plane along selected parallel chords, and $\rho$ sensors $a_5$, $a_6$ are shown positioned in a second pipe 50 with their projections along concentric circles. Each sensor integrates the function $\rho(h)$ dh where h is the coordinate along the path. Dividing by the chord or arc length results in an average $\rho$ along the path. The chord averages may be weighted by well-known mathematical methods to yield a $\rho$ averaged over the entire cross section. Under certain conditions of symmetry of the $\rho$ distribution, the chord averages allows a calculation of the $\rho$ distribution. A circular or 1-turn helical sensor whose projections are equidistant concentric circles tend to weight the $\rho$ profile properly, assuming that for all sensors, the sensitivity per unit length is constant. The spiral $\rho$ sensor $\alpha_7$ shown dashed in the lower pipe of FIG. 9a provides another example of a configuration having uniform sensitivity and whose shape has been designed so that the path length in each annular segment is essentially proportional to the area of that segment.

In FIG. 9b one single $\rho$ waveguide or sensor 16n is located along a selected path, such as the diameter of a circular cross section container or conduit 52 or along the axis. The sensor typically contains impedance discontinuities on junctions to produce echoes between sensor segments $b_1$, $b_2$, $b_3$... The times between successive pairs of echoes can be interpreted in terms of the radial or axial dependence of density, respectively, for the selected paths shown.

As a practical matter, it becomes desirable to control the impedance discontinuities between segments $b_1$, $b_2$... so that the corresponding echo amplitudes are nearly equal. For a $\rho$ profiling probe it will be understood that if the intersegment reflection coefficients R are too small, it will be difficult to accurately measure the time intervals between echoes. But if the R's are too large, there will not be enough energy remaining to interrogate the remote zones. There may also be too much reverberation interference. $R^2$ is a good measure of the potential for errors due to reverberation interference. Table II below contains a few R and $R^2$ values, in terms of the impedance ratio $r = Z_2/Z_1$. The round-trip transmission coefficient $T^2$, and $T^4$ and $T^6$ are also listed.

TABLE II

| r | R | $R^2$ | $T^2$ | $T^4$ | $T^6$ |
|---|---|---|---|---|---|
| 1.35 | .150 | .023 | .978 | .956 | .934 |
| 1.50 | .200 | .040 | .960 | .922 | .885 |
| 2.00 | .333 | .111 | .889 | .790 | .702 |
| 3.00 | .500 | .250 | .750 | .563 | .422 |

If the echoes in sensor 16n are denoted as A,B,C,D..., it can be shown that their respective amplitudes are proportional to R, $RT^2$, $RT^4$, $RT^6$ if R is the same at each joint or discontinuity. As r and R increase, the echo ratio D/A decreases, e.g., about 7%, 11.5%, 30% and 58% for the cases shown.

If the initial r is small enough, say between 1.35 and 2 (convenient rule of thumb, between $\sqrt{2}$ and 2) then the reflection coefficient from one joint to the next are proportionately increased by about the factor $1/T^2$. For example, neglecting attenuation, four approximately equal amplitude echoes are obtained from the reflection coefficient sequence $R_a$, $R_b$, $R_c$, $R_d = 0.200, 0.208, 0.217, 0.228$, respectively. In a sequence of this type, $R_{n-1}/(1 - R_{n-1}^2)$.

At a given joint, say between segments of rectangular cross section, R may be controlled by adjusting b or d or both, or if b and d are held constant, by notching between the segments (FIG. 9b). Discontinuities of controlled reflectivity can be produced by machining a small groove between segments, or by brazing or welding between segments small masses such as a small washer or small bump. FIG. 9b also shows a support such as a 1-turn spiral 42' or radial spiderlegs 42" shown in the circular end view.

Instead of resolving the $\rho$ profile, the profile can be acoustically weighted by nonuniformly contouring the b/d ratio or shape factor and/or constructing a sensor of composite materials, e.g., a bimetallic sensor containing low - and high-density segments. FIG. 9c shows a sensor 16o made of one material but with a variable aspect ratio that is, largest at the walls and circular at the center. The appropriate shape may be derived from the empirical equation or from FIG. 4 in applicant's magnetically with the external coil 26r which encircules the sheath 76. The coil's leads may be soldered to the terminal pins of BNC twinax connector 80 shown screwed into the top of the cap 74. It should be noted that while in some drawings the coil is shown spaced from its associated transducer, the coil may in fact be physically wound on the transducer as shown, for example, in FIG. 1.

The opposed fourth ports of the crosses 70, 70 are plugged by solid pipe plugs 82, 82 whose ends are machined parallel to assure reliable and sufficient coupling between them and external longitudinal wave piezoelectric transducers 84, 84. Suitable transducers 84, 84 are manufactured by Panametrics of Waltham, Massachusetts. Measurement of V based on well-known principles of flow velocimetry.

In cases where the M cell such as that shown in FIG. 10 must be located at a considerably distance from the electronics, or where space is at a premium as in some aircraft engine applications, it becomes important to minimize the number of electrical conductors between the cell and the electronics. Referring to the transducers used in FIG. 10, if the $\rho$ transducers are magnetostrictive, and the V transducers piezoelectric, it will be recognized that their electrical impedances will differ considerably at angular frequencies $\omega = 2\pi f$ which are removed from $\omega_o = \sqrt{1/Lc}$. The V transducers will usually be operated at $f_v \geq 1$ MHz, whereas the $\rho$ transducers will usually be operated near $f_\rho \approx 0.1$ MHz. Two pairs of filters $F_\rho$ and $F_v$ may be connected in series with the corresponding $\rho$ and V transducers. Then a single transmitter conductor may convey simultaneously to the $F_\rho$ and $F_v$ juncture, transmitted waveforms of frequencies $f_\rho$ and $f_v$, and a second receiver conductor can similarly convey simultaneously received waveforms which can be separated and processed by the electronics. Even if the $\rho$ and V transducers are operated sequentially rather than simultaneously, their differing operating frequencies and impedances, and the filters, serve to isolate the $\rho$ and V measurements and confine each to their proper channel within the electronics.

In sensor 16r, the damping or attenuation of extensional waves is typically proportional to the product $\rho\eta$. This provides a way of determining the absolute viscosity coefficient $\eta$ with the $\rho$ sensor. Having determined $\rho$ and $\eta$, the Reynold's number Re is readily calculated for the cell of FIG. 10. It is also possible to measure attenuation of torsional waves in the sensor or in a circular cross section lead in as an alternative measure of the $\rho\eta$ product.

In flowmeter applications where M is to be determined, it is often desirable to eliminate obstructions from the flow path, however small. For this purpose it is possible to use a "dual" of the $\rho$ sensor of the previous configurations, the "dual" consisting of arranging for the fluid (typically a liquid) to pass through an unobstructed sensor instead of requiring the fluid to flow around the sensor. For example, in FIG. 11, a square or rectangular, thin walled tube 86 is the $\rho$ sensor comparable to the sensor 16r. The slow torsional wave is launched by mode conversion as shown but direct launching without mode conversion is also possible. Sensor 86 may also take the form of a square cross section insert in a standard round holed conduit 88. (A noncircular tube may be used as a sensor which is wet both inside and outside by the fluid.)

Also the fluid within such a sensor 86 can be interrogated by longitudinal waves transmitted in a generally axial direction in a manner similar to that shown in FIG. 10, or in a zigzag fashion as indicated by the dashed path in FIG. 11. Either longitudinal interrogating transmission mode would typically use conventional piezoelectric V transducers that are separate from the $\rho$ transducers that are typically magnetostrictive. As before the $\rho$V product is proportional to $\dot{M}$, the mass flow rate.

There are several other ways of using the $\rho$ sensor to obtain V and $\dot{M}$ data. In FIG. 12 the use of two $\rho$ sensors 92, 92 within a conduit 94 is indicated. These sensors are shown orthogonal to the flow, in one plane, and spaced a distance L apart depending on the method used to obtain V and $\dot{M}$ data. Their plane may be the diametrical plane or it may be the midradius plane or other off-axis plane.

As mentioned above, both extensional and torsional modes can be launched in the sensors 92, 92. Due to the Poisson effect, the extensional mode leads to a weak longitudinal wave transmitted between immersed waveguides. By measuring the transit time for this weak wave transmitted first in the upstream direction, then in the downstream direction, V may be determined. Because of the low frequency involved, $f \approx 0.1$ MHz, the small size of the $\rho$ sensors, $d \approx 1$ mm, and the relatively long wavelength in the fluid (e.g., $\lambda \approx 15$ mm in water, $\lambda \approx 10$ to 20 mm in most other liquids) the $\rho$ sensors act similar to line source antennas. Therefore their cross sectional shape is not critical to their radiation pattern and can be optimized for their primary mission, $\rho$ measurement. For aerodynamic reasons a simple radius on leading and trailing edges often suffices. This radiused shape is readily machined, or formed by squeezing in a vise a tube of wall thickness d/2 until the tube collapses to create the desired shape for the $\rho$ sensor (FIG. 12, bottom). The V measurement can also be accomplished using L or S waves in the sensors, especially if at high frequency, $\sim 1$ to 5 MHz, small reflectors are included in the sensors to improve "leakage" between them.

FIG. 12 also illustrates a correlation measurement of V. It is well established that a flowing fluid, particularly a two-phase fluid, contains random inhomogeneities and/or periodic disturbances due to pumping, heat transfer, turbulence, or other reasons. These inhomogeneities tend to propagate at the velocity V. If these inhomogeneities constitute a small $\rho$ difference, then as they pass over each $\rho$ sensor 92, 92, it is possible to measure the time $t_\rho$ between $\rho$ perturbations at each sensor. V may then be calculated as $V = (L+b)/t_\rho$. L would typically be comparable to the diameter D of the conduit 94 for a correlation measurement of V. It will be understood that these $\rho$ sensors 92, 92 could also be oriented axially, obliquely, or otherwise displaced so as to capture the likely $\rho$ perturbations at the V of interest and at the effective pulse repetition frequency in use, if continuous waves are not used.

The $\rho$ sensors can also be used to produce and/or respond to another V-related phenomenon, vortex shedding. As is well known, vortices are shed off struts at a frequency very nearly proportional to V. In the present instance, however, the $\rho$ sensor serves to measure not only $\rho$, but also V, by acting as a vortex shedding frequency meter in one of several unique ways. If the vortices are shed strongly enough, one $\rho$ sensor can either (a) operate passively like an accelerometer, sensing the reaction or lift torque forces as each vortex is shed, or (b) operate actively to sense the periodicity of $\rho$ fluctuations. In cases where the optimum $\rho$ sensor shape is not consistent with the optimum shape for article "Slow Torsional Wave Sensors" in 1977 Ultrasonics Symposium Proceedings, IEEE Cat. #77 CH1264-ISU, pp. 29–34. For a round pipe, or tank which is a right circular cylinder, the sensitivity functions S(r) is in proportion to the radius r. At the center, for example, r=0, and S(r)=0 if the sensor cross section is circular. At the wall, an aspect ratio b/d=3 may be used. The shaping does not have to be the ideal smooth function. A 5- or 10-segment sensor may be an adequate approximation in given practical cases, with each segment having a shape factor or S(r) appropriate for the annular area it senses.

In FIG. 9d sensors $d_1$, $d_2$ of one material and uniform cross section are shown formed into a spiral of constant diameter and variable pitch, or vice versa, respectively. For a spherical tank 54, the pitch of spiral $d_1$ is least at the center and greatest at the top and bottom. The reciprocal of the pitch of $d_1$ may be equated in proportion to $(R_0^2-y^2)$ in order that the integrated $\Delta t$ responds to M, the mass of liquid in the tank where $R_0$ is the radius of the tank 54 and y is the vertical ordinate measured from the center of the sphere. If $\rho$ is uniform, the variable pitch spiral responds to the volume Q of liquid in the container. Again, when $\rho$ is not uniform, the nonuniformly spiraled sensor $d_2$ responds to M. For sensor $d_2$, the helix diameter is made to be in proportion to $(R_0^2-y^2)$. Similar mathematical relationships may be derived to compensate for tanks of other shapes such as elliptical, conical, or truncated sections.

The shape of the nonprismatic tank 56 in FIG. 9e may be compensated by variable shape and/or variable distribution of materials that make a composite sensor. Both approaches are illustrated. The former, exemplified by sensor $e_1$, is readily understood now, as it is similar to the contoured sensor 160 of FIG. 9c. The latter approach, shown by the sensors $e_2$ and $e_3$, may utilize two materials of different density, $\rho_{s1}$ and $\rho_{s2}$, which are compatible with one another and the liquid. For use near room temperature, anodized aluminum and steel could form the bimetallic sensor $e_2$ since their $\rho_{s1}$ and $\rho_{s2}$ differ enough to conveniently provide a variable weighting. To improve symmetry the component of density $\rho_{s1}$ may be sandwiched between a pair of symmetrical components of density $\rho_{s2}$, as indicated by sensor $e_3$. The densities $\rho_{s1}$ and $\rho_{s2}$ preferably differ by at least a factor of two. The sensors of FIG. 9e are designed to yield M directly. By means of purposely-introduced impedance discontinuities the profile may also be determined.

Still referring to FIG. 9e, if the vertical coordinate is designated h, and if the surface area of a differential element of volume dQ is designated s(h), then s(h) is constant for $H_0 \leq h \leq H_1$, and for $h \leq H_2$, but s(h) increases as h increases between $H_1$ and $H_2$. For volumetric weighting, the sensitivity function S(h) should be in proportion to s(h).

Since the sensor can be used to indicate density-dependent parameters such as the mass M of fluid in a column, it can be used for pressure measurement, e.g., as a self-temperature-compensated manometer probe. Sensors 16p and 16q are arranged to accomplish a differential pressure measurement as shown in FIGS. 9f and 9g incorporated in manometers 58, 60, respectively. In the manometer 58, a single transducer 24p launches a torsional wave. Echoes A and B are generated at the beginning and end of the first sensor 16p. At the bottom this sensor, the torsional wave is mode converted to extensional, and then converted back to torsional to interrogate the second sensor 16p, where echoes C and D are generated. The entire U-shaped probe is adjustably supported and sealed through compression fittings 62, 62, such that the sensors 16p, 16p, normally of identical construction, can be positioned with both their tops in the same horizontal plane. The manometer housing includes two vertical stems 64, 64, in which an indicating liquid, typically but not necessarily water, may rise or fall in response to the pressure difference $\Delta P$ between a reference pressure $P_r$ and the unknown pressure $P_x$. The difference in liquid levels is $\Delta H = H_1 - H_2$. $\Delta P = \rho \Delta H$. In some manometers, great effort is devoted to keeping the liquid thermostated so its $\rho$ is constant. This is necessary for high accuracy when H is measured. But in FIG. 9f, $\rho H$ is measured in each leg. That is, with reference to the echo timing diagram of FIG. 9f, $t_{AB} - t_{CD}$ is proportional to $\rho \Delta H$, from which $\Delta t$ is proportional to $\Delta P$. Thus the torsional wave manometer does not require the liquid to be at a known or even constant density. However, temperature effects on $c_{t\phi}$ must be eliminated as discussed above. While one transducer 24p is shown, the two sensors 16p, 16p can be interrogated from separate transducers.

In FIG. 9g, the manometer 60 includes vertical stems 64, 64 that are thin walled square tube sections straddling the extremes of liquid levels $H_{max}$ and $H_{min}$. These square sections 64, 64 are the sensors. They are each interrogated in through-transmission mode. The echo timing diagram shows intervals $t_r$ measured in the reference leg, and $t_x$ in the other leg. Their difference $t_r - t_x$, is proportional to $\rho \Delta H$ which in turn is proportional to $P_x - P_r = \Delta P$.

The ultrasonic densitometer sensor of this invention also lends itself to mass flowmeter applications, particularly ultrasonic mass flowmeter applications where both $\rho$ and V, the flow velocity of the fluid, are to be determined. The mass flow rate $M = \rho V A$ where $A = $ cross sectional area of the conduit in the region where V is measured. Several arrangements intended to illustrate M configurations are shown in FIGS. 10–12.

FIG. 10 shows a sensor 16r positioned within an enclosure that is fabricated of standard pipe 66 and compression fittings 68, 68. The conduit includes the pipe or nipple 66 between two pipe crosses 70, 70. The flow inlet and outlet are via street elbows 72, 72, to simplify an offset installation of this M conduit in an otherwise straight section of pipe. Sensor lead lines 14r, 14r can convey torsional or extensional modes, as illustrated. (In ordinary practice both lead lines would convey the same mode.) The lead lines may be sealed by passing through the compression fittings 68, 68 such as those manufactured by Conax Corp. of Buffalo, N.Y. The magnetostrictive transducers are shown within pipe caps 74, 74 connected to the tops of the fittings. The area bd of sensor 16r is relatively small, typically about 0.5 to 5% of A. The axis of sensor 16r may be angled somewhat relative to the axis of flow in pipe 66 in order to sample $\rho$ over a more representative cross section. However, it will generally be of limited angulation such that its projected area, $A_\rho$, does not exceed 10% of A.

The upper right portion of FIG. 10 also illustrates magnetic coupling between a coil 26r and a magnetostrictive transducer 24r. Within the cap 74 a portion of the magnetostrictive transducer portion is joined to a lead line 14r. A metal sheath 76 whose top is welded closed, is sealed by circumferential weld 78 to the top of compression fitting 68. Transducer 24r communicates vortex shedding, two struts may be utilized. The upstream strut is then shaped to optimize vortex shedding (a bluff body). The downstream strut is simply the $\rho$ sensor 92, sensing both average $\rho$ and $\rho$ fluctuations, the frequency of these fluctuations being proportional to V. Having determined $\rho$ and V, M is readily calculated.

Another passive use of the $\rho$ sensor is to sense the presence or absence of flow, and to a very rough approximation, the numerical value of V, based on flow noise. Thus one combines a measure of $\rho$ with a discrete flow/no flow measurement of V, or with a rough, nonlinear analog measure of V.

If the $\rho$ sensor is heated electrically, a measure of V may be obtained in a manner resembling hot wire anemometry. The temperature of the sensor can be measured ultrasonically by the extensional wave velocity $c_e$, or by electrical resistance, and the local fluid density can be measured by the $\rho$ sensor operating in its torsional mode. These measurements may accompany or follow the applications of heating power to the sensor, so that M can be determined. Likewise, thermal tags may be sensed.

These and other modifications and variations of this invention will become apparent to those skilled in the art from the foregoing detailed description and the accompanying drawings. Such modifications and variations are intended to fall within the scope of the appended claims.

What is claimed and desired to be secured by Letters Patent is:

1. An acoustic system for measuring at least the density-dependent parameter of a fluid, comprising
   transducer means for transmitting and receiving an acoustic wave responding to the torsional mode complex propagation constant $\gamma$,
   a sensor acoustically coupled to said transducer means that propagates said torsional wave axially in a guided mode, said sensor having a noncircular cross section in a plane transverse to said axial direction and being at least partially immersed in said fluid,
   said torsional wave having a velocity of propagation $c_t$ along said immersed sensor portion that is less than the velocity of propagation of said wave along said sensor in a vacuum, and the magnitude of the ratio of said reduction in propagation velocity to said propagation velocity in vacuum being a substantially linear function of the density of said fluid, and
   electronic means for measuring said velocity reduction.

2. A density measuring system according to claim 1 wherein said torsional wave is propagated in said sensor in a travelling mode.

3. A density measuring system according to claim 2 wherein a substantial portion of said sensor is axially curved.

4. A density measuring system according to claim 3 wherein each curved portion of said sensor having a diameter of curvature less than the wavelength of said torsional wave in said sensor extends over an arc length less than ninety degrees.

5. A density measuring system according to claim 3 wherein the arc length of said curved sensor portion is proportional to the area of said fluid associated with each position h on said curved portion where h is a position coordinate measured along said arc length.

6. A density measuring system according to claim 2 wherein said fluid is held in a container and wherein the area of said noncircular cross section varies in said axial direction as a function of the geometry of said container.

7. A density measuring system according to claim 1 wherein said torsional wave is propagated in said sensor in a pulse-echo mode.

8. A density measuring system according to claim 1 wherein said noncircularity of said cross section is sufficiently small to maintain dispersion at less than twenty percent over the bandwidth of said torsional wave.

9. A density measuring system according to claim 8 wherein the length of said sensor in said axial direction is greater than the wavelength $\lambda_s$ of said torsional wave in said sensor, said noncircular cross section is substantially rectangular with a breadth b and a depth d, and $\lambda_s > 4b > 4d$.

10. A density measuring system according to claim 9 wherein the ratio of said sensor length to said wavelength is in the range of 3 to 10.

11. A density measuring system according to claim 9 wherein said torsional wave is a broadband pulse whose duration is less than a round trip travel time for said wave in said sensor.

12. A density measuring system according to claim 8 wherein said noncircular cross section is substantially rectangular and has an aspect ratio of less than 4.

13. A density measuring system according to claim 1 wherein said transducer means includes lead-in means acoustically coupling said transducer means to said sensor, and wherein said lead-in means and said sensor are structured to generate echoes at both ends of said sensor which are approximately equal in magnitude.

14. A density measuring system according to claim 1 wherein the acoustic impedance ratio at the coupling between said transducer means and said sensor is in the range of 1.5 to 4.5.

15. A density measuring system according to claim 1 wherein said sensor is segmented into at least two zones that are axially spaced by junctions.

16. A density measuring system according to claim 15 wherein said sensor segments are collapsed portions of a circular tube and said junctions are uncollapsed portions of said tube.

17. A density measuring system according to claim 15 wherein said probe has n junctions and is structured so that the reflection coefficient $R_n$ at the nth junction is equal to $R_{n-1}/(1-R_{n-1}^2)$.

18. A density measuring system according to claim 17 wherein said acoustic reflection coefficients have a magnitude in the range of 0.15 to 0.50 and each of said coefficients is selected to generate an echo comparable in magnitude to an echo generated by said wave entering said sensor.

19. A density measuring system according to claim 1 wherein the density of said sensor is uniform.

20. A density measuring system according to claim 19 wherein the ratio of the density of said sensor to the density of said fluid is less than ten.

21. A density measuring system according to claim 19 wherein the density of said sensor is less than five grams/cm$^3$.

22. A density measuring system according to claim 1 wherein said sensor has two longitudinally extending components whose densities differ by a factor of at least two.

23. A density measuring system according to claim 1 wherein said fluid is flowing and wherein said sensor is positioned in said flow to generate fluctuations in said wave velocity reduction that are indicative of the velocity of said flow.

24. A density measuring system according to claim 23 wherein said fluctuations are noise pulses having an amplitude and a spectrum that have an empirically determined relationship to said flow velocity.

25. A density measuring system according to claim 23 wherein said fluctuations are oscillatory and at a rate proportional to the frequency at which vortices in said flow are shed proximate to said sensor.

26. A density measuring system according to claim 23 further comprising an additional one of said sensors and means for transmitting and receiving non-torsional ultrasonic longitudinal waves upstream and downstream in said fluid between said sensor and said additional sensor, said sensor and said additional sensor being mutually parallel and oriented substantially perpendicular to said flow.

27. A density measuring system according to claim 23 wherein said fluid flow is in a conduit and further comprising an additional one of said sensors, said sensor and said additional sensor being mutually parallel, oriented perpendicular to said flow and separated by a distance comparable to the hydraulic diameter of said conduit.

28. A density measuring system according to claim 1 further comprising an extensional mode sensor oriented vertically in said fluid and parallel to said torsional wave sensor, means for energizing said torsional wave sensor in the extensional mode, and wherein said electronic means measures the travel time of acoustic leakage over said fluid indicative of the level of said fluid.

29. A density measuring system according to claim 1 further comprising means for measuring the attenuation of said torsional wave in said sensor indicative of the viscosity-density product for said fluid.

30. A density measuring system according to claim 1 wherein said fluid is a liquid and further comprising a manometer tube that holds said liquid, said sensor being partially immersed in said liquid to measure the pressure acting on said liquid.

31. A density measuring system according to claim 30 wherein said manometer has two separate columns, said sensor has two identical segments each partially immersed in said liquid in one of said columns, and said electronic means measures the difference in the travel time of said torsional wave in said sensor segments to indicate the difference in the pressure acting on the liquid in said columns.

32. A density measuring system according to claim 1 further comprising a flow cell in which said fluid flows, and means for generating a longitudinal ultrasonic wave responsive to the flow velocity in a portion of said fluid, and wherein said sensor is immersed in said fluid portion and has a projected area that is less than ten percent of the cross sectional flow area of said flow cell.

33. A density measuring system according to claim 32 wherein said transducer means and said longitudinal wave generating means each include series-connected filters and means for energizing them in parallel including less than three ungrounded conductors.

34. A density measuring system according to claim 1 further including means for compensating for temperature variations in said sensor.

35. A density measuring system according to claim 34 wherein said compensation means comprises forming an axially extending segment of said sensor with a circular cross section.

36. A density measuring system according to claim 34 wherein said compensation means comprises means for transmitting and receiving an extensional wave propagated axially in said sensor and means for measuring the travel time of said extensional wave in a pulse-echo mode.

37. A density measuring system according to claim 34 wherein said compensation means comprises a sensor material having a temperature coefficient of sound speed such that the effect of temperature variations on said torsional wave velocity is less than one percent of the effect of fluid density variations on said torsional wave velocity.

38. A density measuring system according to claim 1 wherein said transducer means includes a magnetostrictive transducer, a metal-sealed enclosure surrounding said transducer, and coil means external to said enclosure that communicates with said transducer.

39. A density measuring system according to claim 1 for step-wise liquid level detection wherein said sensor is rectangular in cross section with an aspect ratio equal to at least two, and is oriented with its larger faces substantially parallel to the surface of said liquid.

40. A density measuring system according to claim 1 for measuring changes in a liquid level, wherein said sensor is substantially straight and is oriented at an angle less than 30° with respect to the surface of said liquid.

41. A density measuring system according to claim 1 wherein said sensor comprises a thin-walled conduit, said fluid is disposed in said conduit, and said reduction in the torsional wave velocity is responsive to the density of said fluid in said conduit.

42. A density measuring system according to claim 1 wherein said fluid is held in a circular conduit and said sensor is substantially straight and disposed in a midradius plane of said conduit.

43. A density measuring system according to claim 1 further comprising an acoustically massive termination secured on at least one end of said sensor.

44. A acoustic system for measuring at least one density-dependent parameter of a non-wetting fluid, comprising transducer means for transmitting and receiving an acoustic wave responding to the torsional mode complex propagation constant $\gamma$ which includes an imaginary attenuation component $\alpha$, a sensor acoustically coupled to said transducer means that propagates said torsional wave axially in a guided mode, said sensor having a noncircular cross section in a plane transverse to said axial direction and being at least partially immersed in said fluid, said torsional wave having an attenuation along said immersed sensor portion that is greater than the attenuation of said wave along said sensor in a vacuum, and the magnitude of the ratio of said increase in attenuation to said attenuation in vacuum being indicative of the density of said fluid adjacent said sensor integrated over said immersed portion of said sensor.

45. A density measuring system according to claim 44 wherein said attenuation $\alpha$ over said immersed portion responds substantially linearly to the density of said fluid.

46. An acoustic system for measuring at least one density-dependent parameter of a non-wetting fluid, comprising transducer means for transmitting and receiving an acoustic wave responding to the torsional mode complex propagation constant $\gamma$, a sensor acoustically coupled to said transducer means that propagates said torsional wave axially in a guided mode, said sensor having a noncircular cross section in a plane transverse to said axial direction and being at least partially immersed in said fluid, said torsional mode propagation constant $\gamma$ being indicative of the integrated density of said fluid adjacent said sensor and at least one part of the torsional mode complex propagation constant $\gamma$ responding substantially linearly to the density of said fluid, said sensor having a length in said direction that is less than fifty times the wavelength $\lambda_s$ of said torsional wave in said sensor, and wherein said noncircular cross section is substantially rectangular with a breadth b and a depth d such that d is less than b and b is less than $\lambda_s/10$.

* * * * *

UNITED STATES PATENT AND TRADEMARK OFFICE
CERTIFICATE OF CORRECTION

PATENT NO. : 4,193,291
DATED : March 18, 1980
INVENTOR(S) : Lawrence C. Lynnworth Page 1 of 2

It is certified that error appears in the above-identified patent and that said Letters Patent are hereby corrected as shown below:

Column 5, line 30, "vaccuum" should be --vacuum--;

Column 7, line 6, "Huntingon" should be --Huntington--;

Column 9, line 27, "vet" should be --yet--;

Column 12, lines 28 and 29, "in vacuo" should be --<u>in vacuo</u>--;

Column 12, line 58, "$\rho$s" should be --$\rho_s$--;

Column 13, lines 41-45, "$\Delta t = k \int_o^H \rho dh = k\rho H = kM$" should be --$\Delta t = k \int_o^H \rho dh = k\rho H = kM$--;

Column 14, line 62, "millemiter" should be --millimeter--;

Column 17, line 53, "h $\leq$ H$_2$" should be --h $\geq$ H$_2$--;

UNITED STATES PATENT AND TRADEMARK OFFICE
CERTIFICATE OF CORRECTION

PATENT NO. : 4,193,291
DATED : March 18, 1980
INVENTOR(S) : Lawrence C. Lynnworth Page 2 of 2

It is certified that error appears in the above-identified patent and that said Letters Patent are hereby corrected as shown below:

Column 19, line 1, "encircules" should be --encircles--;

Column 21, line 6, "M" should be --$\dot{M}$--;

Column 21, line 21, "M" should be --$\dot{M}$--.

Signed and Sealed this

Third Day of August 1982

[SEAL]

Attest:

Attesting Officer

GERALD J. MOSSINGHOFF

Commissioner of Patents and Trademarks